United States Patent
Jenne et al.

(10) Patent No.: US 6,800,436 B1
(45) Date of Patent: Oct. 5, 2004

(54) DIAGNOSTIC METHOD, DIAGNOSTIC REAGENT AND THERAPEUTIC PREPARATION FOR DISEASES CAUSED BY VARIATION IN LKB1 GENE

(75) Inventors: Dieter E. Jenne, Neuried (DE); Jun-ichi Nezu, Niihari (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/555,166

(22) PCT Filed: Nov. 27, 1998

(86) PCT No.: PCT/JP98/05357

§ 371 (c)(1),
(2), (4) Date: Nov. 27, 2000

(87) PCT Pub. No.: WO99/28459

PCT Pub. Date: Jun. 10, 1999

(30) Foreign Application Priority Data

Nov. 27, 1997 (JP) .............................. 9-344256
Oct. 1, 1998 (JP) .......................... 10-280357

(51) Int. Cl.[7] .............................................. C12Q 1/68
(52) U.S. Cl. .......................... 435/6; 436/503; 436/504; 436/64; 536/24.3
(58) Field of Search .............................. 536/24.3, 23.1, 536/24.32, 23.5; 436/503, 504, 64; 435/6

(56) References Cited

U.S. PATENT DOCUMENTS 5,709,999 A * 1/1998 Shattuck-Eidens et al. ..... 435/6
5,827,726 A   10/1998 Nezu ...................... 435/252.33

OTHER PUBLICATIONS

GenEmbl accession number AF032985 (Jan. 28, 1998).*
Giradiello, et al. 1987, New England J of Medicine, 316:1511–14.*
Spigelman, et al. 1989, Gut. 30:1588–90.*
GenBank Accession Number AAT38290, May 14, 1997.
Tomlinson et al., "Peutz–Jeghers syndrome", 1997, J Med Genet, vol. 34;1007–1011.
Hemminki et al., "Localization of a susceptibility . . . ", 1997, Nat Genetics, vol. 15(1);87–90.
Jishage et al., "Role of Lkb1, the causative gene of Peutz–Jegher's . . . ", 2002, Proc Natl Acad Sci USA, vol. 99(13);8903–8.
Jenne et al. "Peutz–Jeghers syndrome . . . ," Nature Genetics, 18:38–43, 1998.
Bignell et al., "Low Frequency of . . . ," Cancer Research, 58:1384–1386, 1998.
Hemminki et al., "A serine/threonine . . . ," Nature, 391:184–187, 1998.
Walsh, J.H., Gastroenterology, 114:429 1998.
Avizienyte et al., "Somatic Mutations in . . . ," Cancer Research, 58:2087–2090, 1998.
Wang et al., "Genetic Pathways of . . . ," American Journal of Pathology, 153(2), 363–366, 1998.
Stratakis et al., "Carney Complex . . . ," J. Clin. Endocrinol. and Metab., 83(8):2972–2976.
Nakagawa et al., "Nine novel . . . ," Hum. Genet., 103:168–172, 1998.
Dong et al., "Frequent Somatic . . . ," Cancer Research, 58:3787–3790, 1998.

* cited by examiner

Primary Examiner—Larry R. Helms
Assistant Examiner—Misook Yu
(74) Attorney, Agent, or Firm—Fish & Richardson P.C.

(57) ABSTRACT

With respect to a range of 1.5 Mbp and more in the chromosome 19p13.3 region containing Peutz-Jeghers gene, a continuous cosmid contig is constructed and a restriction map is prepared. Next, genes mapped with this region are searched by using EST database and the locations of these genes are accurately determined. Based on the evaluation of biological data, etc., several highly likely candidates for Peutz-Jeghers genes are specified from the genes thus found. After successively analyzing variations in these genes in DNAs of patients with Peutz-Jeghers syndrome, it is found that one of these genes, i.e., "LKB1" has been specifically varied in these patients. Thus, the diseases caused by the variation in the LKB1 gene can be diagnosed and treated by using the LKB1 gene, primers and probes based on its base sequence, LKB1 protein, an antibody biding to this protein, etc.

13 Claims, 10 Drawing Sheets

DIAGNOSTIC METHOD, DIAGNOSTIC REAGENT AND THERAPEUTIC PREPARATION FOR DISEASES CAUSED BY VARIATION IN LKB1 GENE

CROSS REFERENCE TO RELATED APPLICATIONS

This application claims priority under 35 U.S.C. § 371 from PCT International Application No. PCT/JP98/05357, filed Nov. 27, 1998, which claims priority from Japanese Application No. 10/280357, filed Oct. 1, 1998 and Japanese Application No. 9/344256, filed Nov. 27, 1997.

TECHNICAL FIELD

The present invention relates to a method of diagnostic of the diseases caused by mutations in the LKB1 gene and to an diagnostic reagent and a therapeutic preparation for said diseases.

BACKGROUND ART

Peutz-Jeghers (PJ) syndrome [MIM 175200] is an autosomal dominantly inherited disorder characterized by melanotic pigmentation of lips, perioral and buccal regions and by benign, hamartomatous and adenomatous types of multiple gastrointestinal polyps. Patients with this syndrome are known to frequently develop benign or malignant neoplasms in the gastrointestinal tract, pancreas, ovaries, testis, breast and uterus. In particular, small benign tumors frequently occur in the ovary and are developed as multifocal, symmetrical germinal-cord structures with annular tubules. Then, they progress into granulosa cancer and result in ambisexual precocity in girls. It was found that multifocal germinal cord cancer in boys, though with low frequency, results in gynecomasty and feminization due to overproduction of estrogen. Defects in the gene responsible for Peutz-Jeghers syndrome (PJ gene) appear to predispose to a wide spectrum of neoplastic diseases. In fact, 50% of the carriers with a defect in one of PJ allele are known to develop cancer by the age of 60 (Giardiello, F. M. et al. Increased risk of cancer in Peutz-Jeghers syndrome. N. Engl. J. Med. 316,1511–1514 (1987); Spigelman, A. D., Murday, V. & Phillips, R. K. Cancer and Peutz-Jeghers syndrome. Gut 30, 1588–1590 (1989). [MIM 175200]). It is believed that loss or inactivation of the PJ gene product results in disruption of the fundamental growth control mechanism within somatic cells that have potential high proliferative capacity, which triggers the growth of benign hamartomatous polyps some of which turn into malignant tumor cells after further genetic alteration.

Recently, it was reported that PJ gene was mapped to chromosome 19p13.3 by linkage analysis in 12 families of PJ syndrome with a multipoint lod score of 7.00 at the microsatellite genetic marker D19S886 (Hemminki, A. et al. Localization of a susceptibility locus for PJ syndrome to 19p using comparative genomic hybridization and targeted linkage analysis. Nat. Genet. 15 (1), 87–90 (1997)). A similar linkage between PJ gene and the genetic marker D19S886 was reported in a second study investigating five other families as well (with a multipoint lod score of 7.52) (Amos, C. I. et al. Fine mapping of a genetic locus for PJ syndrome on chromosome 19p. Cancer Res. 57, 3653–3656 (1997)). D19S565 was first known as a genetic marker proximal to the PJ gene, which causes recombination with the gene. Thereafter, the genetic marker D19S878 was found to be located more proximal to the gene. These two makers, therefore, were thought to define the proximal border of the PJ candidate region. In both linkage studies, no recombination was observed between the marker D19S886 and PJ gene, indicating that they are located in a narrow interval.

DISCLOSURE OF THE INVENTION

An objective of the present invention is to identify the gene responsible for Peutz-Jeghers syndrome and to provide a method for diagnosing diseases resulting from a mutation in this gene, a diagnostic reagent and a therapeutic preparation for the diseases.

To identifiy the gene for PJ syndrome, the present inventors made a continuous cosmid contig and a restriction map for the region extending from 1.5 Mb within chromosome 19p13.3 which includes the PJ gene. EST database search for the genes mapped in this region was then performed, and the precise locations of these genes were determined. The inventors evaluated biological information of a number of genes thus found and selected several potent candidates of the PJ gene. Mutation analysis of these candidate genes in DNAs from patients with PJ syndrome revealed that one of the candidate genes, "LKB1," was specifically mutated in the patients with PJ syndrome. Thus, the inventors' intense investigations successfully identified the gene responsible for PJ syndrome for the first time. Based on this finding, the inventors found that diseases caused by mutations in the LKB1 gene can be diagnosed and treated by utilizing the LKB1 gene, primers and probes based on the sequence thereof, LKB1 protein and antibodies that bind to LKB1 protein.

As described above, the present invention relates to a method of diagnosing diseases caused by mutation in the LKB1 gene, the gene responsible for PJ syndrome, and to a diagnostic reagent and a therapeutic preparation for the diseases. More specifically, the present invention relates to:

(1) a primer DNA used for diagnosing a disease caused by mutation in the LKB1 gene, the primer DNA comprising a nucleotide sequence containing at least a portion of any one of the nucleotide sequences shown in SEQ ID NOs: 1 to 4;

(2) the primer DNA according to (1), wherein the primer DNA has a nucleotide sequence corresponding to any one of the nucleotide sequences shown in SEQ ID NOs: 7 to 30;

(3) the primer DNA according to (1) or (2), wherein the disease caused by mutation in the LKB1 gene is Peutz-Jeghers syndrome;

(4) a probe DNA used for diagnosing a disease caused by mutation in the LKB1 gene, the probe DNA comprising a nucleotide sequence containing at least a portion of any one of the nucleotide sequences shown in SEQ ID NOs: 1 to 4;

(5) the probe DNA according to (4), wherein the disease caused by mutation in the LKB1 gene is Peutz-Jeghers syndrome;

(6) a therapeutic preparation for a disease caused by mutation in the LKB1 gene, the preparation comprising the LKB1 gene as an active ingredient;

(7) a therapeutic preparation for a disease caused by mutation in the LKB1 gene, the preparation comprising the LKB1 protein an active ingredient;

(8) a therapeutic preparation for a disease caused by mutation in the LKB1 gene, the preparation comprising a compound that enhances the activity of LKB1 protein as an active ingredient;

(9) the therapeutic preparation according to (6) to (8), wherein the disease caused by mutation in the LKB1 gene is Peutz-Jeghers syndrome;

(10) a reagent for diagnostic of a disease caused by mutation in the LKB1 gene, the reagent comprising an antibody that binds to the LKB1 protein as an active ingredient;
(11) the reagent according to (10), wherein the disease caused by mutation in the LKB1 gene is Peutz-Jeghers syndrome;
(12) a method of diagnosing a disease caused by mutation in the LKB1 gene, the method comprising detecting mutation in the LKB1 gene;
(13) a method of diagnosing a disease caused by mutation in the LKB1 gene, the method comprising the steps of:
(a) preparing a DNA sample from a patient;
(b) amplifying the DNA using the primer DNA according to (1);
(c) cleaving the amplified DNA;
(d) fractionating the DNA fragments according to their size;
(e) hybridizing the probe DNA according to (4) with the fractionated DNA fragments; and
(f) comparing the size of the DNA fragment thus detected to that from a control of a healthy subject;
(14) a method of diagnosing a disease caused by mutation in the LKB1 gene, the method comprising the steps of:
(a) preparing a RNA sample from a patient;
(b) fractionating the RNA sample depending on its size;
(c) hybridizing the probe DNA according to (4) with the RNA thus fractionated;
(d) comparing the size of the RNA thus detected to that from a control of a healthy subject;
(15) a method of diagnosing a disease caused by mutation in the LKB1 gene, the method comprising the steps of:
(a) preparing a DNA sample from a patient;
(b) amplifying the DNA using the primer DNA according to (1)
(c) separating the amplified DNA into single stranded DNA;
(d) fractionating the separated single stranded DNA on a non-denatured gel;
(e) comparing the mobility of the single stranded DNA separated on the non-denatured gel to that of a control of a healthy subject;
(16) a method of diagnosing a disease caused by mutation in the LKB1 gene, the method comprising the steps of:
(a) preparing a DNA sample from a patient;
(b) amplifying the DNA using the primer DNA according to (1);
(c) fractionating the amplified DNA on the DNA denatured gradient gel;
(d) comparing the mobility of the fractionated DNA on the gel to that of a control of a healthy subject;
(17) the method according to any one of (12) to (16), wherein the disease caused by mutation in the LKB1 gene is Peutz-Jeghers syndrome.

The present invention was made based on the inventors, findings that Peutz-Jeghers syndrome is caused by a mutation in the gene called "LKB1". The present invention primarily relates to the use of polynucleotides containing at least a portion of the nucleotide sequence corresponding to the genomic DNA coding LKB1 (including intron, promoter, and enhancer regions as well as exon regions), and said polynucleotides for diagnosing diseases resulting from mutations in the LKB1 gene. The genomic DNA regions of LKB1 are shown in the SEQ ID: 1 to 4. The sequences shown in SEQ ID: 1 to 4 correspond to 5' upstream region, exon 1 and intron 1 (a part) region, exons 2 to 8 and introns 1 (a part) to 8 (a part) region, and intron 8 (a part) and exon 9 region of the LKB1 gene, respectively.

Nucleotide sequences containing a portion of these regions can be used as primers or probes to diagnose the diseases resulting from mutations in the LKB1 gene. A nucleotide used as a primer is typically 15 to 100 bp, preferably 17 to 30 bp. Any primer can be used as long as it amplifies at least a portion of the LKB1 gene or regions regulating the gene expression. Such regions include, for example, exon, intron, promoter, and enhancer regions of the LKB1 gene. On the other hand, nucleotides used as a probe typically have a sequence of at least 15 bp or more when the nucleotides are synthetic oligonucleotides. Double stranded DNA obtained from a clone into which a vector such as plasmid DNA is incorporated can be used as a probe. For a region utilized as a probe, any part of the LKB1 gene or region regulating the expression thereof can be used. Such regions include, for example, exon, intron, promoter and enhancer regions of the LKB1 gene. When used as a probe, oligonucleotide or double stranded DNA is used after adequately labeling. Labeling methods, for example, include labeling of the 5'-terminus by phosphorylating with $^{32}$P using T4 polynucleotide kinase, and labeling by incorporation of substrate bases labeled with isotopes such as $^{32}$P, fluorochrome or biotin using DNA polymerases such as Klenow enzyme and primers such as random hexamer oligonucletides (random-primer method).

The diseases detectable using these nucleotides, which are caused by mutations in the LKB1 gene are not limited to Peutz-Jeghers syndrome. Any disease caused by mutations in the LKB1 gene is included. PTEN and APC genes were discovered as causative genes for Cowden's disease, which is one of hereditary cancers, and Familial Adenomatous polyposis (FAP), respectively. Both genes proved to be mutated with high frequency in the non-hereditary common cancers. PTEN and APC genes function to control cell proliferation in the normal tissues, and it is believed that a critical step in tumorigenesis occurs when these genes mutate and lose their functions resulting in cells escaping from the regulation of these genes. Similar to PTEN and APC genes, a mutation in the LKB1 gene possibly plays a part in common tumorigenesis.

The diagnostic method of the diseases caused by mutations in the LKB1 gene in the present invention features detection of mutations in the LKB1 gene. In the present invention, by the term "the diagnosis of the diseases caused by mutations in the LKB1 gene" is meant not only the testing of patients who have developed the particular symptoms resulting from a mutation in the LKB1 gene, but also testing a mutation in the LKB1 gene for determining whether the subject has a predisposition to the particular disease resulting from a mutation in the LKB1 gene. A mutation in one of allele of the LKB1 gene is thought to largely increase the risk for a particular disease caused by mutations in the LKB1 gene even if the symptom has not apparently been developed. The present invention also includes a diagnostic method for identifying patients who have a mutation in one of allele of the LKB1 gene (carriers). "Detection of a mutation in the LKB1 gene" in the present invention includes detection in DNA, RNA and protein.

One embodiment of the diagnostic method of the present invention is a method of directly determining the nucleotide sequence of the LKB1 gene of a patient. For example, sequencing is performed after amplifying the whole or a partial sequence of the LKB1 gene of a patient using a technique such as PCR (Polymerase Chain Reaction), using the nucleotides described above as primers, and the DNA isolated from a patient who is suspected of being afflicted with a disease caused by a mutation in the LKB1 gene, as template. The sequence thus determined can be used to diagnose the diseases caused by mutations in the LKB1 gene by comparing it to the sequence of the LKB1 gene from healthy subjects.

In addition to the methods as described above in which DNA from a patient is directly sequenced, different methods can be used as diagnostic methods of the present invention. One of such embodiments comprises the steps of (a) preparing DNA samples from patients, (b) amplifying the DNA from the patients using the primer DNA of the present invention, (c) separating the amplified DNA into the single stranded DNA, (d) fractionating the single stranded DNA separated on non-denaturing gel, and (e) comparing the mobility of the single stranded DNA separated on the gel to that of a control of ordinary person.

Such methods include PCR-SSCP (single-strand conformation polymorphism; polymorphism of single-stranded DNA in higher-order structure) method (Cloning and polymerase chain reaction-single-strand conformation polymorphism analysis of anonymous Alu repeats on chromosome 11. Genomics. 1992 Jan. 1; 12(1): 139–146., Detection of p53 gene mutations in human brain tumors by single-strand conformation polymorphism analysis of polymerase chain reaction products. Oncogene. 1991 Aug. 1; 6(8): 1313–1318., Multiple fluorescence-based PCR-SSCP analysis with postlabeling., PCR Methods Appl. 1995 Apr. 1; 4(5): 275–282.). Having the advantage of relatively simple manipulation and smaller sample volume requirement, this method is particularly suitable for screening a large number of DNA samples. The principles of the method are as follows: when double stranded DNA fragments are denatured into single stranded DNA, each single stranded DNA forms an original higher-order structure peculiar to its nucleotide sequence; these denatured DNA, even if they are complementary to each other and have the same chain-length, migrate to distinct positions according to their conformation when electrophoresed on a non-denaturing polyacrylamide gel; the conformations of these single stranded DNA are altered by substitution of a single nucleotide and the substituted DNA migrate with different mobility by electrophoresis on polyacrylamide gel; and thus, detection of the alteration in the mobility enables the detection of mutations such as point mutation, deletion or insertion in the DNA fragment of the interest.

In the PCR-SSCP method, the whole or a portion of the LKB1 gene is initially amplified using a technique such as PCR. A nucleotide sequence ranging in length from about 200 to 400 bp is typically preferred as a fragment to be amplified. Portions to be amplified include an exon, intron, promoter and enhancer of the LKB1 gene. PCR can be performed under the conventional conditions (for example, the conditions used for amplification of each exons using the primers shown in example 5). On amplifying the gene fragment by PCR, DNA fragments to be synthesized in the PCR reaction may be labeled with primers labeled with an isotope such as $^{32}P$, fluorochrome or biotin, or by adding substrate nucleotides labeled with an isotope such as $^{32}P$, fluorochrome or biotin in the PCR reaction solution. The said DNA fragments may also be labeled by adding substrate nucleotides labeled with an isotope such as $^{32}P$, fluorochrome or biotin to the synthesized DNA fragments by using Klenow enzyme after the PCR reaction. The labeled DNA fragments thus obtained are denatured by heat, for example, and electrophoresed on a polyacrylamide gel without any denaturing agent, such as urea. As to the electrophoresis, conditions for fractionating DNA fragments can be improved by adding an appropriate amount of glycerol (5 to 10%) to polyacrylamide. Conditions for electrophoresis vary depending on the nature of each DNA fragment. Electrophoresis is typically performed at room temperature (20 to 25° C.), but when preferable fractionation is not obtained, in the temperature ranging from 4 to 30° C., it is better to test the optimal mobility to determine the temperature which gives the most desirable mobility. After the electrophoresis, mobility of the DNA fragment is detected and analyzed by autoradiography using X-ray films and by scanner for detection of fluorescence. When the bands with different mobility are detected, those bands are directly dissected from the gel, re-amplified by PCR, and subjected to direct sequencing to confirm the mutation. In case where DNA fragments synthesized by PCR are not labeled, the bands of said DNA fragments may be detected using staining techniques such as ethidium bromide or silver staining.

Another embodiment of the diagnostic methods of the present invention comprises the steps of (a) preparing a DNA sample from a patient, (b) amplifying the DNA derived from the patient using the DNA primers of the present invention, (c) cleaving the DNA thus amplified, (d) fractionating the DNA fragments depending on their size, (e) hybridizing the DNA fragments thus fractionated with the probe DNA of the present invention, and (f) comparing the length of the DNA fragment thus detected to that from healthy subjects.

These methods include the methods utilizing restriction fragment length polymorphism (RFLP) and PCR-RFLP method. These methods are based on the principle that when a mutation has occurred in the recognition site for a restriction enzyme or when insertion or deletion of bases has occurred in the DNA fragments generated by treatment with a restriction enzyme, the length of those fragments treated with the restriction enzyme generally deviates from that of normal subjects. In fact, for Peutz-Jeghers syndrome, in the LKB1 gene of the four patients shown as samples, D, B, MA and FA, with Peutz-Jeghers syndrome, acquisition of ScaI site, elimination of AhdI, RsaI, and BsrBI site had occurred, respectively (Table 3). Therefore, these mutations can be detected as the differences of bands' mobility after electrophoresis, which was performed after the portions containing these mutations are amplified by PCR and then treated with the restriction enzymes mentioned above. Alternatively, the mutations can be detected by subjecting DNA from patients to southern blotting using the probe DNA of the present invention, after the DNA is treated with these restriction enzymes and electrophoresed. Restriction enzymes used other than those mentioned above are properly selected depending on each mutation. In this method, besides detecting the mutations via restriction enzyme treatment of genomic DNA prepared from patients, cDNA prepared by the treatment of RNA prepared from patients with reverse transcriptase is directly treated with the restriction enzyme and then can be used for southern blotting to detect mutations. This cDNA can also be used as a template for PCR, and the amplified product thereof (the whole or a portion of the LKB1 gene) can be digested with a restriction enzyme and then electrophoresed to detect mutations shown as difference of mobility of the DNA fragments.

RNA prepared from patients may be used for the detection instead of DNA. Such a method comprises the steps of (a) preparing an RNA sample from a patient, (b) fractionating the prepared RNA depending on the size, (c) hybridizing the RNA thus fractionated to the DNA probe of the present invention, and (d) comparing the size of the RNA fragment thus detected to that from normal subjects. Specifically, RNA prepared from a patient is electrophoresed and subjected to northern blotting to detect the difference of mobility.

Other embodiments of the diagnostic methods of the present invention comprise the steps of (a) preparing a DNA sample from a patient, (b) amplifying the DNA derived from the patient using the primers of the present invention, (c) fractionating the amplified DNA by electrophoresis on the denaturing gradient gel, (d) comparing the mobility of the DNA on the gel fractionated to that from normal subjects.

A similar method includes denaturant gradient gel electrophoresis (DGGE) method. In this method, the whole or a portion of the LKB1 gene is amplified by PCR using primers of the present invention, for example, and electrophoresed on the polyacrylamide gel in which the concentration of a denaturant such as urea gradually increases as the DNA migrate through the gel. The mobility of the DNA is compared to that of normal subjects. If a DNA fragment contains a mutation, it comes to be melted into single stranded DNA in the point of lower denaturant concentration and is remarkably retarded in mobility, and detection of such difference of mobility allows detection of a mutation.

Besides these methods, allele specific oligonucleotide (ASO) hybridization method can be used for the purpose of only detecting only a mutation in a specific position. In this method, an oligonucleotide containing sequence supposed to have a mutation is synthesized and hybridized with a DNA sample. If the DNA sample has a mutation, the efficiency of hybridization decreases, and this decrease is detected using techniques such as southern blotting and the method of utilizing the florescence quenching property of specific florescent reagents, which are quenched when intercalated into the gap between the hybrids.

Ribonuclease A mismatch cleavage may also be used for the detection. In this method, the whole or a portion of the LKB1 gene is amplified by PCR, for example, and the amplified DNA is subjected to hybridization with labeled RNA prepared from LKB1 cDNA or and such, which is inserted into a plasmid vector and such. This hybrid forms single stranded structures at the sites of mutation, and said sites may be cleaved by ribonuclease A and then detected using some method such as autoradiography. Presence of mutations, can be thus detected.

The present invention relates to a diagnostic reagent for diseases caused by mutations in the LKB1 gene, wherein the reagent comprises, as an active ingredient, an antibody, which binds to the LKB1 protein. Antibodies, which bind to LKB1 protein, can be prepared according to methods well known in the art. As for polyclonal antibodies, for example, a small animal such as a rabbit is immunized with the LKB1 protein (a natural protein as well as a recombinant KLB1 protein expressed in suitable host cells (*E. coli*, yeast or mammalian cells), such as LKB1 protein expressed as a fusion protein with GST in *E. coli*) or its partial peptide (for example, peptide composed of amino acid sequence shown in the SEQ ID: 31 or 34) to obtain antiserum, which then can be purified and prepared using a method such as ammonium sulfate precipitation, protein A, protein G column, DEAE ion exchange chromatography, affinity columns coupled with LKB1 protein or synthetic peptide. For monoclonal antibodies, for example, a small animal such as a mouse is immunized with LKB1 protein or a part of the peptide, and then dissected to remove the spleen. The spleen is homogenized to isolate the cell fraction. These cells are fused with mouse myeloma cells and a reagent such as polyethylene glycol to create fusion cells (hybridomas). From the hybridoma cells thus generated, an appropriate clone which produces an antibody which binds to LKB1 protein is selected. Subsequently, the hybridoma cells thus obtained are intraperitoneally transferred into a mouse, ascites is harvested from the same mouse, and the monoclonal antibody thus obtained can be prepared by purifying by means of, for example, ammonium sulfate precipitation, protein A, protein G column, DEAE ion exchange chromatography, affinity columns coupled with LKB1 protein or synthetic peptide.

When used as a reagent, the antibody is, if necessary, mixed with sterile water, physiological saline, vegetable oils, surface active agent, lipids, solubility increasing agent, stabilizers (e.g. BSA and gelatin), and preservatives and such. In a test using said antibody, a tissue or cells from a patient are stained using a method such as enzyme-labeled or fluorescence-labeled antibody technique to detect deficiency, aberrant accumulation, or unusual intracellular distribution of LKB1 protein. Alternatively, the protein, which is fractionated from cell extracts prepared from a tissue or cells from patients with Peutz-Jeghers syndrome using a method such as SDS-PAGE, is transferred onto a membrane such as nitrocellulose or PVDF, and detected using a staining method such as enzyme-labeled technique above (western blotting, immunoblotting).

By constructing a detailed physical map of 19p13.3 region, the inventors revealed that the disease-related gene LKB1 for Peutz-Jeghers syndrome is located in the close proximity of a microsatellite marker D19S886, i.e. their distance on chromosome is about 190 kb. Therefore, the loss of heterozygosity (LOH) test utilizing D19S886 marker may effectively serve as a test for diagnosing various diseases based on mutations in the LKB1 gene.

The present invention also relates to a therapeutic preparation for diseases caused by mutations in the LKB1 gene. In one embodiment, it comprises the LKB1 gene as an active ingredient. When the LKB1 gene is used as a therapeutic preparation, the whole or a portion of the genomic LKB1 DNA, or the LKB1 cDNA (SEQ ID: 5) is incorporated into an appropriate vector, such as adenovirus vector, adenoassociated virus vector, retrovirus vector, and plasmid DNA, and administered orally, intravenously, or topically to the patient. As a method of administration, ex vivo administration can be used as well as in vivo administration. In administration of a drug, enclosing the gene into a liposome generated by micellization of phoshpholipids can enhance the mobility and intake of the gene into the tissue. Alternatively, cationic lipids may be added to form a complex with DNA, which can enhance the mobility and intake of the gene into the tissue. Using these methods, the LKB1 gene mutated in the patient can be substituted by a normal gene, or the normal gene can be additionally administered to the patient, resulting in the possible treatment of a disease caused by a mutation in LKB1 gene.

Another embodiment of a therapeutic preparation for the diseases caused by mutations in the LKB1 gene, comprises the LKB1 protein as an active ingredient. The LKB1 protein may be prepared as a natural protein or a recombinant protein by utilizing a recombinant DNA technology. The amino acid sequence of the LKB1 protein is shown in SEQ ID: 6. A natural protein may be isolated using well-known methods. For example, it can be isolated from the cultured cells of the testis, fetal liver or K562 cell, in which the LKB1 protein is expressed at a high level, and by affinity column chromatography using an antibody against a partial peptide of the LKB1 protein described in Example 7. On the other hand, a recombinant protein can be prepared by culturing cells transformed by DNA (SEQ ID: 5) encoding LKB1 protein. Cells that can be used to produce a recombinant protein include mammalian cells, such as COS, CHO, and NIH3T3 cells; insect cells, such as Sf9 cells; yeast; and *E.* coli. The vectors suitable for expressing a recombinant protein intracellularly depend on the host cells, for example, pcDNA3 (Invitrogen) or pEF-BOS (Nucleic Acids. Res. 1990, 18(17), p.5322) vector is used for mammalian cells; "BAC-to-BAC baculovirus expression system" (GIBCO BRL) for insect cells; "Pichia Expression Kit" (Invitrogen) for yeast; and pGEX-5X-1 (Pharmacia) and "QIAexpress system" (Quiagen) for E. coil. The vectors can be introduced into the host cells by a well-known method such as the calcium phosphate method, DEAE dextran method, the method using cationic liposome DOTAP (Boehringer Mannheim) or SuperFect (Quiagen), electroporation, and calcium chloride. A recombinant protein thus obtained can be purified using a conventional technique, for example, the method described in "The Qiaexpressionist handbook, Quiagen, Hilden, Germany".

When the LKB1 protein obtained is used as a therapeutic preparation for diseases caused by mutations in the LKB1 gene, the LKB1 protein can be directly administered, or can be given after formulating by a well-known pharmaceutical process. For example, formulations may be administered in proper combination with a pharmaceutically acceptable carrier or medium, such as sterile water, physiological saline, vegetable oils, surfactants, lipids, dissolving adjuvants, stabilizers, or preservatives. While the dosage for administration differs depending on various factors, such as weight, age, and health conditions, or the method of administration, a person skilled in the art will be able to advantageously select the appropriate dosage. Typically, the dosage is in the range of 0.01 to 1000 mg/kg. Administration can be conducted, for example, orally, intravenously, intramuscularly or subcutaneously.

A person skilled in the art can easily carry out substitution, deletion, addition and/or insertion of amino acids in the amino acid sequence of the LKB1 protein for the purpose of improving the activity and stability of the drug of the present invention, utilizing a well-known method, such as PCR-based site-directed mutagenesis (GIBCO-BRL, Gaithersburg, Md.), site-directed mutagenesis using oligonucleotides (Kramer, W. and Fritz, H J (1987) Methods in Enzymol., 154:350–367), the Kunkel's method (Methods Enzymol. 85, 2763–2766 (1988)). A similar altered LKB1 protein can also be used as a therapeutic preparation of the present invention.

Another embodiment of a therapeutic preparation for diseases caused by mutations in the LKB1 gene, the therapeutic preparation comprises a compound, which enhances the activity of the LKB1 protein, as an active ingredient. The LKB1 gene encodes a serine threonine kinase that shows as high as 82% homology with XEEK1 serine threonine kinase from Xenopus. A collapse of the serine threonine kinase activity of the LKB1 protein is closely associated with the emergence of diseases resulting from mutations in the LKB1 gene. Therefore, it is envisaged that enhancement of the said serine threonine kinase activity will serve to treat diseases caused by mutations in the LKB1 gene.

A screening method for a compound that enhances the activity of the LKB1 protein is as follows. For example, LKB1 proteins expressed in E. coli as a fusion protein with GST, or those expressed in mammalian or insect cells, are used to determine kinase activities of these proteins in the presence of the test compound, to select a compound that enhances the activity of the LKB1 protein.

More specifically, for example, phosphorylation activity of a substrate protein for the LKB1 protein, or autophosphorylation activity of the LKB1 protein may be determined by measuring the transfer of $^{32}P$ from $[\gamma$-$^{32}P]$ATP to the substrate in an appropriate reaction solution (e.g. 50 mM Tris-HCl, pH 7.2, 1 mM dithiothreitol (DTT), 10 mM MgCl2, 10 mM $MnCl_2$, and so on), using a device, such as a liquid scintillation counter, and thus a compound which enhances the activity of LIB1 protein can be isolated by selecting a compound that increass the $^{32}P$ transfer level. Like the LKB1 protein used as therapeutic preparation as described above, the isolated compound may be formulated using well-known pharmaceutical processes to be administered for treatment of a disease. Typically, the dosage is in the range of 0.01 to 1000 mg/kg.

In addition to the methods as described above, a method utilizing the regions regulating the LKB1 gene expression, or a factor binding to the gene can be used for treatment of the diseases caused by mutations in the LKB1 gene. The present invention has revealed the structure of the LKB1 gene and the 5' upstream region thereof (SEQ ID: 1). This 5' upstream region may contain the regions regulating the LKB1 gene expression (e.g. promoters and enchancers), and a person skilled in the art could easily specify genetic regions regulating the LKB1 gene expression, using several known methods in combination. A method for specifying the region regulating gene, for example, comprises the following steps: (a) constructing a vector in which a reporter gene is joined to downstream of the 5' upstream region of the LKB1 gene (DNA composed of the whole or a portion of sequence shown in SEQ ID:1); (b) introducing said vector into appropriate cells; and (c) detecting the activity of the reporter gene. Specifically, the upstream region of the LKB1 gene is cleaved into appropriate sized fragments, for example, by various restriction enzymes, and these fragments are integrated into the upstream site of a reporter gene, such as a firefly luciferase, secretory alkali phosphatase, or chloramphenicol acetyltransferase (CAT) gene to construct expression vectors (PicaGene™ Vector, Wako Pure Chemicals Industries, Ltd). Subsequently, these expression vectors are introduced into appropriate host cells, such as COS, HEK293, and CHO cells, and then incubated for a certain interval. After the incubation, the intracellular and extracellular reporter gene product expression is separately measured to determine the promoter activity of the individual gene fragment integrated into the vector. Once a gene fragment showing the promoter activity is identified, such a fragment may further be cleaved into smaller fragments and subjected again to the same process as described above to define the active site to a more specified region. To finally confirm the active site, the nucleotide sequence of the region specified as the active site may be altered by, for example, site-directed mutagenesis and the activity is measured. The region regulating the LKB1 gene expression is particularly useful in the gene therapy described above, since it can direct the expression of the LKB1 gene in vivo, under natural expression control, when this region is joined to the upstream of the normal LKB1 gene described above and then administered to a patient whose LKB1 gene is mutated.

In addition, once the promoter region is defined in the upstream of the LKB1 gene, screening for compounds that can regulate the LKB1 gene expression may be easily facilitated by investigating effects on the production of the reporter gene product using reporter gene expression vectors with this site and various compounds. Such screening method comprises the steps of: (a) constructing a vector in which a reporter gene is joined to downstream of the promoter region of the LKB1 gene; (b) introducing said vector into appropriate cells; and (c) detecting the activity of the reporter gene by exposing a test compound to the said cells and/or introducing the compound into the said cells. Test compounds include, but are not limited to, proteins, peptides, synthetic compounds, natural compounds, genes, and gene products and such.

Screening for compounds that can regulate the LKB1 gene expression may be carried out by exposing a test sample to the promoter region and selecting the compound (e.g. a protein) that binds to said promoter region. For instance, transcriptional regulatory factors which control the LKB1 gene expression and bind to this promoter can be purified using affinity-purification by, creating a synthetic oligo-DNA and such containing the promoter sequence, binding this to a suitable supporting-agent, such as cellulose, and exposing it to a cell-extract and such.

Additionally, the inventors have revealed that neoplasia, such as polyps, develop as a result of a mutation in the LKB1 gene in the patients with Peutz-Jeghers syndrome. This finding lead to a notion decreasing in the amount or activity of the LKB1 protein can render normal cells temporary cell proliferation activity. Therefore, the artificial reduction in the amount or activity of the LKB1 protein, which is achieved by utilizing anti-sense DNA for the LKB1 gene or the cDNA thereof, or by utilizing a compound which inhibits the activity of the LKB1 gene, will possibly serve to treat the diseases which require fresh cell proliferation, such as wound curing and anagenesis.

BEST MODE FOR CARRYING OUT THE INVENTION

Figures 1A, 1B:
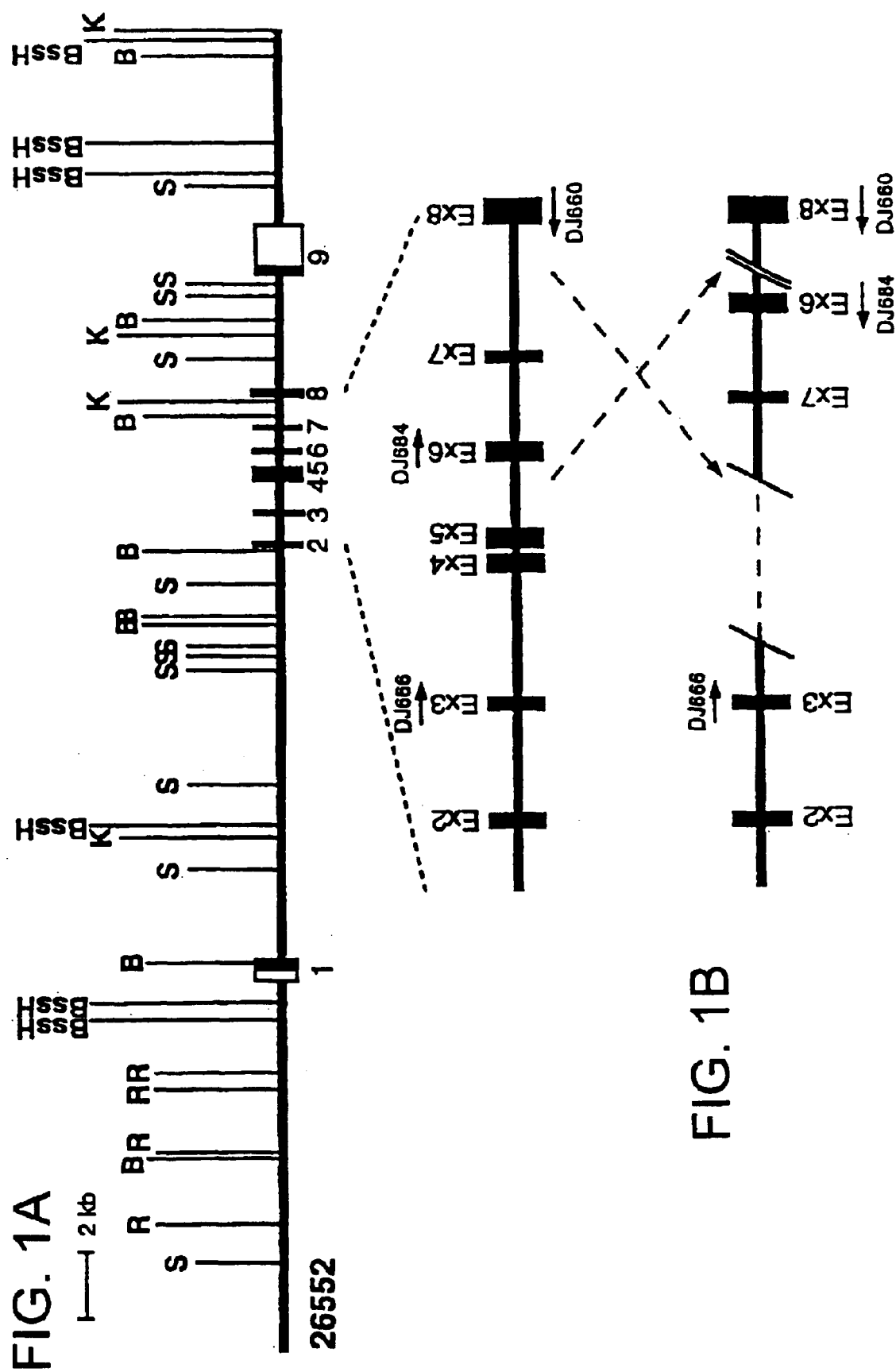
FIG. 1a illustrates the chromosomal organization of the LKB1 gene and the adjacent regions together with the restriction enzyme map, wherein R indicates EcoRI site; B, BamHI; S, SacI; K, KpnI; BssH, BssHII. Nine exons of the LKB1 gene were indicated by boxes. Closed and open boxes represent the translated and untranslated regions, respectively.
FIG. 1b shows a schematic illustration of gene rearrangement found in Peutz-Jeghers patient A. The upper part of the panel shows the organization of the normal-type LKB1 gene; the bottom part shows the organization of the mutant-type gene from Peutz-Jeghers patient A. The orientations and the positions of the primers used in PCR analysis are shown by arrows.

The present invention will be described further in detail by referring to the examples below, but is not to be construed as being restricted thereto.

EXAMPLE 1

Construction of a Cosmid Clone Contig Covering a Region on Human Chromosome 19p13.3

In order to identify efficiently all the genes located in the region of human chromosome 19p13.3, a contig of contiguous clones (contig of arranged clones) assembled with cosmid clones and other clones was constructed. Suitable cosmid clones were selected from a group of clones mapped in this region by FISH, having short and different overlapping regions; and gaps between the clones were successively filled with clones obtained by screening cosmid, phosmid and BAC libraries (cosmid walking, chromosome walking). A high-resolution physical map was, thus, prepared by constructing a contig of the contiguous clones covering a 1.5 Mbp region on chromosome 19pter.

Specifically, the contig was constructed as described below. A short contig of cosmid clones covering a region on chromosome 19p13.3, which was mapped and alligned previously by FISH (Ashworth, L. K. et al. An integrated metric physical map of human chromosome 19. Nature Genet. 11, 422–427 (1995)), was further extended using genomic clones obtained from chromosome 19-specific cosmid libraries with Lawrist5 vector as well as Lawrist16 vector, a chromosome 19-specific phosmid library with pBeloBac11 vector, and an entire human genome cosmid library (Stratagene) as well as an entire human genome BAC library (Research Genetics). The cosmid walking was started from the ends of two contigs each containing the PRNT3 gene locus (Zimmer, M. et al. Three human elastase-like genes coordinately expressed in the myelomonocyte lineage are organized as a single genetic locus on 19pter. Proc. Natl. Acad. Sci. U.S.A. 89, 8215–8219 (1992)) or the GZMM gene locus (Pilat, D. et al. The human Met-ase gene (GZMM): structure, sequence and close physical linkage to the serine protease gene cluster on 19p13.3. Genomics, 24, 445–450 (1994)) on 19p13.3. Specifically, overlapping clones were successively obtained by screening using the EcoRI fragments derived from the ends of the contigs as probes; the high-density filters of the cosmid and phosmid libraries were treated with Cot1 DNA (New England Biolabs) for background reduction. In some cases, nucleotide sequences of the insert ends were determined directly using the cosmid clones as sequence templates; the primers used were Llawrist vector-specific primers, DJ180 (SEQ ID NO: 35/CGACTCACTATAGGGAGACCCA) and DJ181 (SEQ ID NO: 36/CCTCGAGAATTACCCTCACTAA). The sequences determined were utilized: (i) to search the databases for the identification of novel genes exhibiting significant homologies to known genes; (ii) to prepare STS (Sequence Tagged Site) which is used for further experiments of chromosome walking. Thus, the contig was assembled from cosmid clones covering a 1.5 Mbp region near the telomere on chromosome 19. Restriction sites of BamHI, BssHII, EcoRI, HindIII, RpnI, and SacI were mapped on the cosmid clones, to prepare a restriction enzyme map of the region. More specifically, the map construction was carried out by the following procedures: the cosmid DNAs were linearized by treatment with lambda terminase and by partial digestion using restriction enzymes; the cos sites of the DNAs were labeled, and subsequently digested with restriction enzymes; the map was made based on the length of each restriction fragment (cos-site labeling method; Rackwitz, H. R., et al. Analysis of cosmids using linearization by phage lambda terminase. Gene 40, 259–266 (1985)).

EXAMPLE 2

Identification of Genes Mapped on the Cosmid Clone Contig on 19p3.3

Previously, by radiation hybrid mapping method, 91 clones of EST (Expressed Sequence Tag) have been mapped in a region more proximal to the telomere than the genetic marker, D19S216, on 19p3.3. Clones of EST overlapping one another were removed by analyzing the sequences using a software program, UNIGENE, (http://www.ncbi.nlm.nih.gov/UniGene/index.html), and as a consequence, 60 clones of EST were finally identified to be derived from independent genes. Primer sets for amplifying the respective ESTs were purchased from Research Genetics; the cosmid clones belonging to the previously constructed contig on 19p3.3 were categorized into four non-overlapping groups; then the locations of the respective genes were assigned on the contig by PCR screening. When an EST gave the positive signal, then the databases were searched for other overlapping ESTs to extend the sequence of the EST. Complementary DNAs corresponding to the respective positive ESTs were purchased from Research Genetics; using the inserts of the cDNAs as probes, EcoRI-digested cosmid clones were analyzed by Southern hybridization, to determine the accurate positions of the respective genes in the contig.

The accurate position of genetic marker D19S886 (GenBank accession number: Z52881) was also determined in this cosmid clone contig. Specifically, a DNA fragment containing the marker sequence was prepared from the human total DNA by PCR amplification using the sense primer (SEQ ID NO: 37/TGGATCTACACTCCGGC) and the antisense primer (SEQ ID NO: 38/ATTTTACTGGCTGGCACTTG); the cosmid clone, R32184, was digested with EcoRI, SacI, BamHI, or BssHII, and then the digest was subjected to Southern-blot analysis using the DNA fragment as a probe, to determine the accurate position of the marker on the EcoRI map.

Moreover, mouse genes mapped previously in a region of mouse chromosome 10, which corresponds to human 19p, were mapped on this contig by similar procedures. Furthermore, new genes contained in this contig were identified by searching databases such as LLNL database [http://www-bio.llnl.gov] with the sequences of the cosmid ends.

EXAMPLE 3

Identification of a Candidate Region Containing the Peutz-Jeghers Gene

Earlier linkage studies have reported that a candidate region for the Peutz-Jeghers gene may be located more proximally to the telomere than markers D19S878 and D19S565; however there was no reported marker located on the telomere side of these markers at all, and accordingly the candidate region was assumed to span over a genomic region of as long as approximately 2 Mb or more on the telomere side of the markers. Nonetheless, there was the possibility that the mutant gene was located very near this marker, considering the close linkage of D19S886 marker and the Peutz-Jeghers gene locus. Thus, the accurate position of marker D19S886 was first determined in the cosmid contig as described above, and then the neighboring genes were diagnosed. The result showed that there were 21 genes within the region of 400 kbp neighboring to marker D19S886. Candidates for the causative gene of Peutz-Jeghers syndrome were selected from the newly identified genes, based on a wide variety of biological information such as information obtained by the analyses of the counterpart genes of other species. The samples of chromosomal DNA prepared from Peutz-Jeghers patients were diagnosed for nucleotide mutations within the respective genes selected.

EXAMPLE 4

Identification of the LKB1 Gene and the Analysis of Genomic Organization thereof The GenBank database was searched for the sequences exhibiting homologies to cosmid clone R29114 at its end on the telomere side, which was contained in the contig spanning over a region on 19p3.3; the result showed that the cosmid end shared a short sequence of 32 bp with a cDNA (GenBank accession number: U63333) encoding a novel human serine-threonine protein kinase (LKB1). The cosmid clone was directly sequenced using primers, DJ649 (SEQ ID NO: 24) corresponding to the 5' end of the LKB1 cDNA sequence and DJ650 (SEQ ID NO: 29) corresponding to the 3' end; clone R29114 and the adjacent clone R26552 contained the LKB1 gene, and thus it was clarified that the LKB1 gene was located in this region. For the determination of the entire exon-intron organization of the LKB1 gene and for further analyses in detail, PCR primers and sequence primers (shown below; Tables 1 and 2) were designed, based on the LKB1 cDNA sequence (1302 bp). Sequences of the respective gene segments were determined by direct sequencing of the PCR products amplified from the cosmid DNAs. The sequences obtained were compared with the LKB1 cDNA sequence to identify positions of the exons and the splice junctions of all the introns. Each exon position on the restriction map was determined by comparing the positions of restriction sites in the genomic sequence and by comparing the distances, estimated by long distance PCR, between the respective segments of the gene (FIG. 1a). Nucleotide sequence was determined by bi-directional sequencing in almost all the regions except for prominently long introns 1 and 8.

Figure 2:
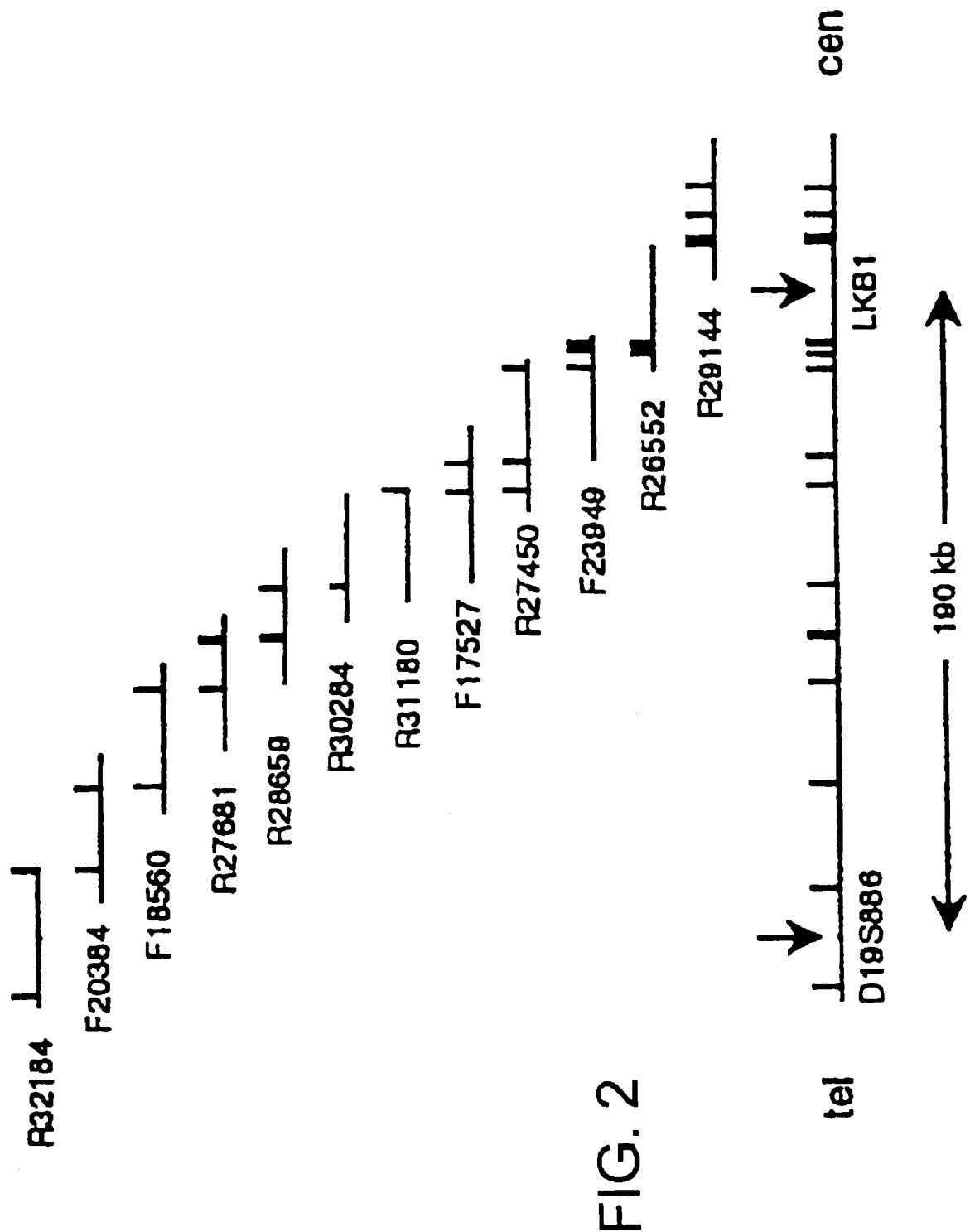
FIG. 2 shows a contig of cosmid clones in the region neighboring to the position of microsatellite marker D19S886, and the map of EcoRI site in the region. The bottom shows a schematic illustration of positional relationship between the LKB1 gene and microsatellite marker D19S886 in the region of human chromosome 19p13.3; tel denotes the direction to the telomere; cen, the direction to the centromere. The upper part of the panel shows the partially overlapping, arranged cosmid clones.

The result showed that the LKB1 gene spanning over 23 kb or more was split into 9 coding exons and a non-coding exon. Moreover, the gene was presumed to be transcribed toward the direction from the telomere to the centromere (FIG. 2); interestingly, the splice junction of intron 2 was revealed to violate the GT/AG rule characteristic of ordinary intron-exon junctions. The sequence of intron 2 starts with "ATATCCCTT" at the 5' end and terminates with "CCCAC"; the "TCCTTAAC" motif is located 15 bp upstream of exon 3. These three sequence elements have close similarities to those of the eukaryotic intron which has been recently reported to be as a very rare intron. Introns with this sequence pattern are spliced in a U12 snRNA-dependent manner, which is not the general way of splicing.

EXAMPLE 5

Analysis of Mutations in Patients Affected with Peutz-Jeghers Syndrome

Sequences of the primers used for the mutation analysis of the patients affected with Peutz-Jeghers syndrome are shown in table 1 below.

Mutation analysis was carried out using DNA samples from five unrelated patients affected with Peutz-Jeghers syndrome (patients A, B, D, MA and FA). The deletion and rearrangement of the gene were screened by long distance PCR using the primer sets, DJ659 and DJ660, and DJ666 and DJ660.

Figure 3A:
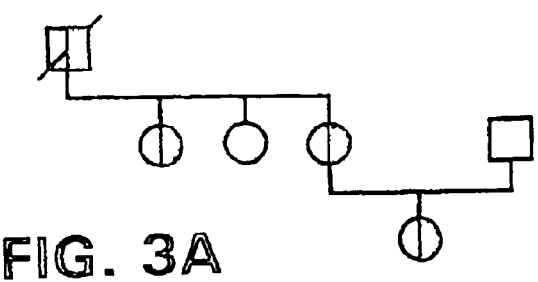
FIG. 3a displays the pedigree of patient A expanding three generations. The symbol in which the right half is filled indicates an affected member.
Figure 3B:
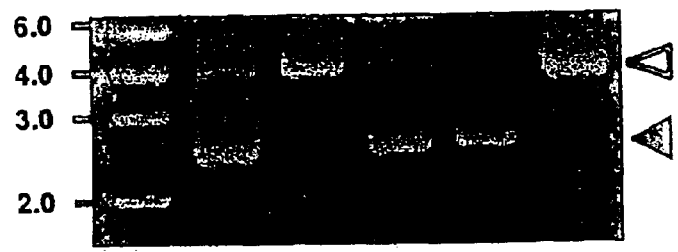
FIG. 3b shows the result obtained by long distance PCR with primers, DJ666 and DJ660. An aberrant type of PCR products of 2.5 kbp, which is indicated by a filled triangle, is observed only in the affected family members.
Figure 3C:
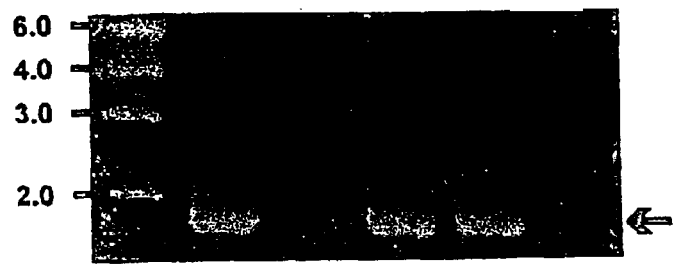
FIG. 3c shows the result obtained by PCR analysis with primers, DJ666 and DJ684. The amplification of the PCR products is observed only in the affected members, which indicates that an inversion exists in the corresponding region.

All the DNA samples derived from the patients and healthy normal persons as controls gave the products of 3.9 kbp in the PCR amplification with the primer set of DJ666 and DJ660. However, not only the 3.9 kbp products but also the products of 2.5 kbp were found in the sample of Peutz-Jeghers patient A (FIG. 3b). The shorter DNA fragment was subcloned, sequenced and then compared with the chromosomal DNA sequence of the normal counterpart; the result showed that the LKB1 gene was complicatedly rearranged in the chromosome of this patient (FIG. 1b). Specifically, the PCR products of 2.5 kbp had two deletion mutations; one is a deletion of a 1286 bp segment located between intron 3 and intron 5, and the other is a deletion of an 81 bp segment located inside intron 7. The longer deletion contains exons 4 and 5. In addition to this, an inversion was found in the central region containing exons 6 and 7. The existence of the inversion was confirmed by PCR analysis using sense primers, DJ666 and DJ684, which were specific to exon 3 and exon 6, respectively. Both of these primers correspond to the sense chain, and therefore PCR products are given only when the inversion exists. The analysis has revealed that the inversion is carried by all the affected family members, including patient A, for two generations. On the other hand, this mutation was found neither in the healthy members of the same family nor in unrelated healthy normal persons used as controls (FIGS. 3a and 3c).

The complicated LKB1 mutation was analyzed at the level of transcripts by RT-PCR using RNA prepared from the cells of peripheral blood of patient A. The RNA was isolated using an RNA Isolation Kit (Qiagen) and reverse-transcribed into cDNA using Superscript (GIBCO-BRL, Life Technologies). Two distinct PCR products of 730 bp and 270 bp were given by PCR using a primer set of DJ660 and DJ666. There is a length difference of about 460 bp between the two types of the PCR products; the length agrees well with the length between exon 4 to exon 7 in the transcript, suggesting the production of the transcript from which the segment of exons 4 to 7 has been removed by splicing, and which was presumed to be caused by the complicated mutation. The aberrant splicing event, in which exon 3 directly links to exon 8, does not result in frameshift, but the resulting transcript is assumed to encode an aberrant protein consisting of 281 amino acids in which the C-terminal half of the catalytic domain is missing.

Figure 4:
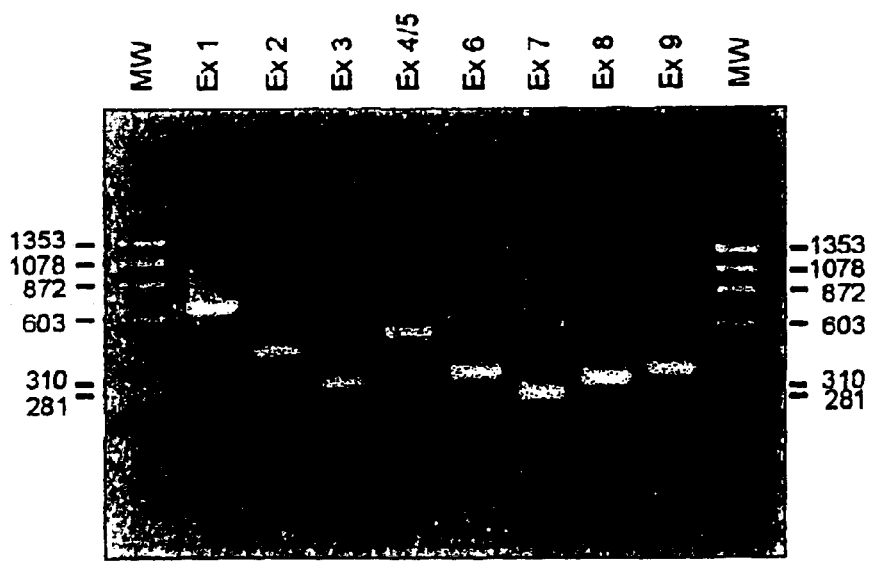
FIG. 4 shows the pattern of agarose gel electrophoresis of LKB1 exons amplified by PCR. Exon Numbers are indicated on the top. MW represents the molecular weight marker.

The aberrant PCR products were not observed in any of patients B, D, MA, and FA. Eight sets of primers were designed for the screening of point mutations in the LKB1 gene (Table 2); the respective exons were amplified independently and then directly sequenced (FIG. 4).

TABLE 1

| DJ705 | 5'-GGGAATTCGGAACACAAGGAAG-3' | (SEQ ID NO: 23/exon 1) |
| DJ649 | 5'-ATGGAGGTGGTGGACCCGC-3' | (SEQ ID NO: 24/exon 1) |
| DJ659 | 5'-GTTACGGCACAAAAATGTCATCCA-3' | (SEQ ID NO: 25/exon 2) |
| DJ666 | 5'-GGTGATGGAGTACTGCGTGTG-3' | (SEQ ID NO: 26/exon 3) |
| DJ684 | 5'-ACATCGGGAAGGGGAGCTACG-3' | (SEQ ID NO: 27/exon 6) |
| DJ660 | 5'-CCGGGCACCGTGAAGTCCTG-3' | (SEQ ID NO: 28/exon 8) |
| DJ650 | 5'-TCACTGCTGCTTGCAGGCC-3' | (SEQ ID NO: 29/exon 9) |
| DJ717 | 5'-GCAGGCGGCCAGCCTCA-3' | (SEQ ID NO: 30/exon 9) |

TABLE 2

| | | |
|---|---|---|
| DJ698 | 5'-GGTCCCCGAGGACGAAGTTGA-3' | (SEQ ID NO: 7/exon 1 sense) |
| DJ673 | 5'-ACCATCAGCACCGTGACTGG-3' | (SEQ ID NO: 8/exon 1 antisense) |
| DJ703 | 5'-TCGCCGGCCGATGACAGA-3' | (SEQ ID NO: 9/exon 2 sense) |
| DJ674 | 5'-AAGGAGACGGGAAGAGGAGCAG-3' | (SEQ ID NO: 10/exon 2 antisense) |
| DJ690 | 5'-GAGGAGGGGCAAGGTGGGT-3' | (SEQ ID NO: 11/exon 3 sense) |
| DJ680 | 5'-GTGTGGCCTCACGGAAAGGAG-3' | (SEQ ID NO: 12/exon 3 antisense) |
| DJ692 | 5'-AGCTGGGCCTGTGGTGTTTG-3' | (SEQ ID NO: 13/exon 4–5 sense) |
| DJ694 | 5'-CAGAGGCCCCTCGGAGTGTG-3' | (SEQ ID NO: 14/exon 4–5 antisense) |
| DJ695 | 5'-GCCTCTGTCCCTGGGGTAGA-3' | (SEQ ID NO: 15/exon 6 sense) |
| DJ693 | 5'-TCAGTCCTCTCAATGCCTGCTG-3' | (SEQ ID NO: 16/exon 6 antisense) |
| DJ696 | 5'-GCGGGGTCCCCCTTAGGAG-3' | (SEQ ID NO: 17/exon 7 sense) |
| DJ697 | 5'-CTAGCGCCCGCTCAACCAG-3' | (SEQ ID NO: 18/exon 7 antisense) |
| DJ675 | 5'-GGAGCTGGGTCGGAAAACTGGA-3' | (SEQ ID NO: 19/exon 8 sense) |
| DJ702 | 5'-TGCTCCCGTGGGACATCCTG-3' | (SEQ ID NO: 20/exon 8 antisense) |
| DJ676 | 5'-GTAAGTGCGTCCCCGTGGTG-3' | (SEQ ID NO: 21/exon 9 sense) |
| DJ677 | 5'-GTGGCATCCAGGCGTTGTCC-3' | (SEQ ID NO: 22/exon 9 antisense) |

Since the intron between exon 4 and exon 5 is short, the exons were amplified together at the same time. The result showed that all the patients carry mutations in one of the two alleles of the LKB gene. The result is shown in Table 3. Codon numbers in the table indicate the last wild-type codon. Restriction enzyme sites were diagnosed for the presence of mutations in the PCR products of the Peutz-Jeghers patients as well as healthy normal persons. The symbols, + and −, accompanying the names of restriction enzyme indicate the presence and absence of the site, respectively. Nucleotides of LKB1 genes derived from patients B, MA and FA have been numbered on referring to nucleotide numbers assigned in the LKB1 cDNA sequence deposited in GenBank (accession number: U63333). Nucleotide numbers used in the LKB1 sequence from patient D are indicated on referring to those of the LKB1 gene sequence deposited in GenBank (accession number: AF032985).

at amino acid position 239. In patient D, the di-nucleotide AG to be conserved strictly at the splice acceptor site located at the 3' end of intron 3 was found to be altered to AA. When exon 4 is skipped and as a result exon 3 links to exon 5, a frameshift occurs immediately behind amino acid position 155 and the protein sequence terminates at amino acid 241. It was found that, in patient FA, nucleotide G at nucleotide position 843 (exon 6) was deleted, which caused a frameshift and the generation of a stop codon, TGA, at nucleotide 857.

All the mutations found in the LKB1 gene of the five patients affected with Peutz-Jeghers syndrome result in loss of the indispensable part in the kinase domain, and as a consequence the conformation is presumed to be destroyed in the mutant LKB1 proteins. In addition, the C-terminal amino acids, which were assumed to constitute the regulation domain in LKB1 protein, were missing in the four of these patients. These mutations in the LKB1 gene were

TABLE 3

| Patient | Mutation type | Mutation position | Codon | Restriction site | Possible influence |
|---|---|---|---|---|---|
| A | inversion/deletion | exon 4–7 | 155 | | deletion of codons 156–307 |
| D | G2412A | intron 3 | 156 | +ScaI | deletion of splice acceptor site exon 4 skipping; frameshift premature termination at codon 242 |
| B | deletion of GGTC at nucleotide position 716 | exon 5 | 240 | −AhdI | premature termination at codon 285; frameshift |
| MA | C759A | exon 6 | 252 | −RsaI | Tyr253 (TAC)→ Stop codon (TAA) |
| FA | deletion of G at nucleotide position 843 | exon 6 | 280 | −BsrBI | frameshift; premature termination at codon 286 |

In patient MA, C is substituted for A at nucleotide position 759 (in exon 6), and as a result, TAC codon of tyrosine is altered to a stop codon, TAA, at amino acid position 253. It was revealed that, in patient B, four base pairs from nucleotide position 717 to 720 (in exon 5) were deleted; the deletion results in the generation of a stop codon at the position 135 bp downstream from the codon for tryptophan considered to give rise to the loss of kinase activity in the LKB1 proteins as mutant gene products, and the signal transduction pathway in which LKB1 was involved was blocked as a consequence.

The genomic organization of the LKB1 gene was similarly investigated in a Japanese patient affected with polyposis who was suspected of Peutz-Jeghers syndrome (SK1).

The genomic DNA was extracted from the peripheral blood of the patient using a QIAamp Blood kit (Qiagen), and the LKB1 gene was amplified by PCR using the DNA as a template and using the primers indicated in Table 2. The result of direct sequencing analysis of the PCR products showed that there was a single-base (C) deletion (the C is the third nucleotide of codon "GAC" corresponding to Asp at amino acid position 207) in the coding region within exon 5. The mutation results in a frameshift on the C-terminal side of Asp 207, which perhaps generates a truncated protein without the kinase activity as a result.

The PCR amplification of the LKB1 gene derived from the DNA sample was performed basically under the following conditions: the reaction solution, of which total volume was 50 μl, contained 100 ng of chromosomal DNA (template DNA), 50 pmol of primer, PCR buffer J (Invitrogen), 2.5 units of AmpliTaq (Perkin Elmer), and 2.5 μl of DMSO, or the solution contained 100 ng of chromosomal DNA (template DNA), 20 pmol of primer, 5 μl of 10× TaKaRa Taq buffer (TaKaRa), 4 μl of 2.5 mM dNTPs (TaKaRa), 0.4 μl of TaKaRa Taq DNA polymerase (TaKaRa), and 0.4 μl of Taqstart™ Antibody (CLONTECH); the reaction profile was: pre-heat at 94° C. for 2 to 4 minutes; 35 cycles of denaturation at 94° C. for 30 to 45 seconds, annealing at 58° C. or 62° C. for 30 seconds and extension at 72° C. for 45 seconds; and the final extension at 72° C. for 3 minutes. The resulting PCR products were purified using a QIAquick Gel Extraction kit (Qiagen) after agarose gel electrophoresis, or purified from the PCR reaction solution using a QIAquick Nucleotide Removal kit (Qiagen); using the purified PCR products as a template, direct sequencing was performed bidirectionally. A Drhodamine terminator cycle sequencing kit (Applied Biosystems) was used in the sequencing.

In order to verify that the mutations found were not caused by artifacts in PCR amplification or in sequencing, DNAs covering the regions containing the mutations were amplified by PCR under the conditions described above, the resulting PCR products were digested with restriction enzymes selected for the respective mutations, and then the lengths of the fragments obtained by the digestion were diagnosed for the mutation sites (PCR-RFLP analysis). Specifically, a 20 μl reaction solution consisting of 5 μl of PCR products, 4 units of restriction enzyme (AhdI, BsrBI, RsaI or scaI) and 2 μl of restriction enzyme buffer was incubated at 37° C. for 1.5 hours; the resulting lengths of the DNA fragments were analyzed by agarose electrophoresis.

Figure 5:
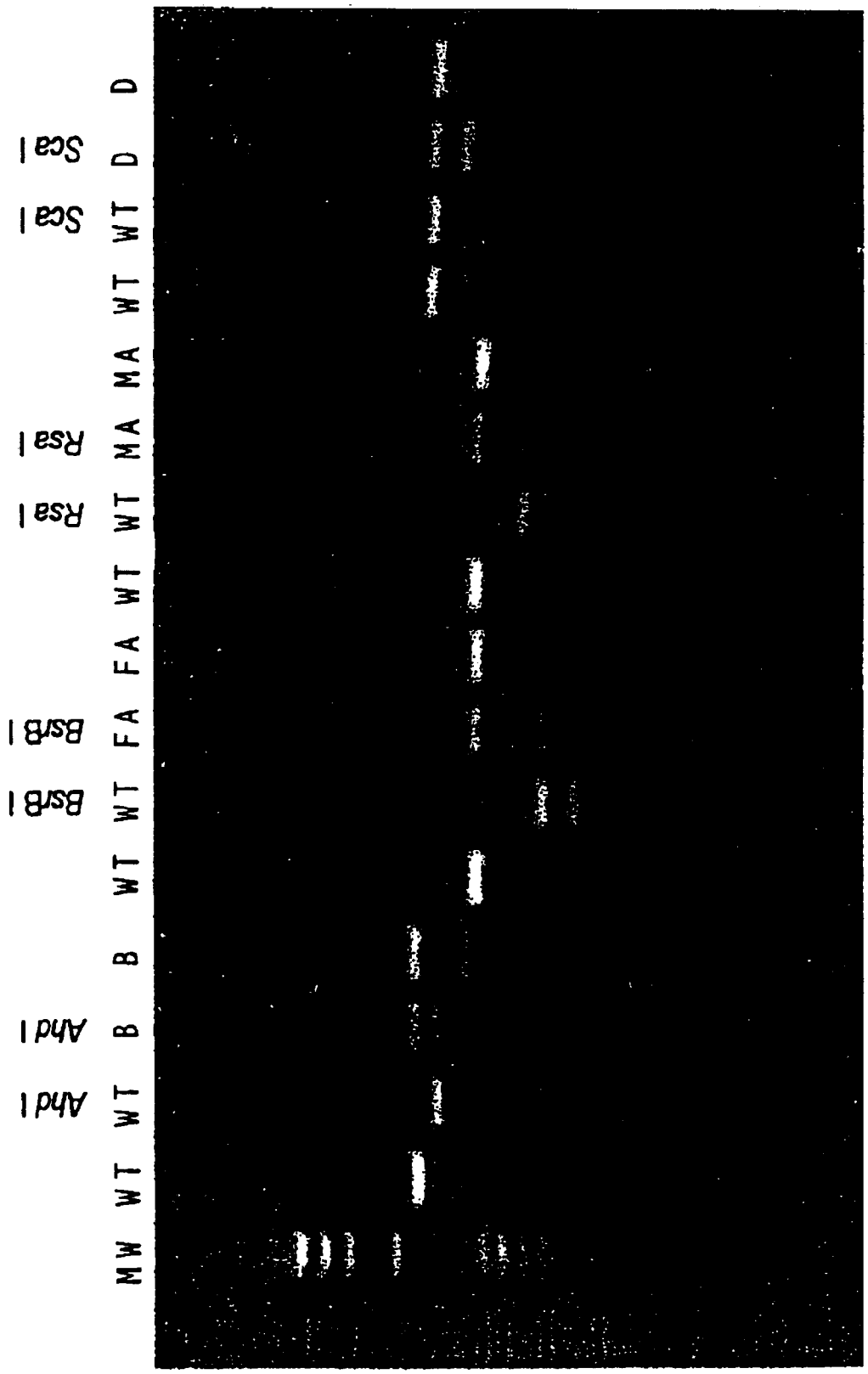
FIG. 5 shows an electrophoretic pattern obtained by PCR-RFLP analysis. The marks, AhdI, BsrBI, RsaI, and ScaI on the pattern indicate the samples treated with the corresponding restriction enzymes shown. WT denotes a DNA sample from a healthy normal person; B, Peutz-Jeghers patient B; FA, Peutz-Jeghers patient FA; MA, Peutz-Jeghers patient MA; D, Peutz-Jeghers patient D. MW indicates the molecular weight marker.

When the DNA samples from 50 healthy persons were diagnosed by the same analysis, the mutations were not observed in these samples at all; thus the results showed that the mutations were specific to patients with Peutz-Jeghers syndrome (FIG. 5).

EXAMPLE 6

Construction of Plasmid DNAs for the Expression of the LKB1 Gene in E. coli and Mammalian Cells A DNA fragment encoding the entire LKB1 amino acid sequence with a c-Myc epitope sequence (SEQ ID NO: 41/Glu Gln Lys Leu Ile Ser Glu Glu Asp Leu) as a C-terminal tag was amplified by PCR using the LKB1 cDNA clone as a template and using LK E1 primer (SEQ ID NO: 39/5'-gat gaa ttc ggg tcc agc atg gag gtg gtg gac-3') and LK E2 primer (SEQ ID NO: 40/5'-gat gaa ttc tta gag gtc ttc ttc tga gat gag ctt ctg ctc ctg ctg ctt gca ggc cga-3'); the PCR products were digested at the EcoRI sites located within the primer sequences; the EcoRI fragment was inserted into pcDNA3 vector (Invitrogen) at the EcoRI site for the expression in mammalian cells or into pGEX-5X-1 vector (Pharmacia) at the site for the expression in E. coli. The cloned DNAs were diagnosed by sequencing not to have any sequence variations as artifacts caused by PCR amplification; and such clones were selected and used for expression experiments.

In vitro mutagenesis was carried out using pcDNA3/LKB1myc as a template and using GeneEditor™ (Promega), to prepare expression plasmid DNAs with the mutations corresponding to the amino acid substitutions found in the Peutz-Jeghers patients. Specifically, the expression plasmid DNA (pcDNA3/LKB1 D176Nmyc) for D176N mutation (the abbreviation means the substitution mutation from Asp to Asn at amino acid 176; the mutations shown below are also abbreviated in the same way) was constructed by introducing the mutation using LK D176N primer (SEQ ID NO: 45/5'-att gtg cac aag aac atc aag ccg ggg-3'); the plasmid for mutation W308C (pcDNA3/LKB1 W308Cmyc), LK W308C primer (SEQ ID NO: 46/5'-cgg cag cac agc tgc ttc cgg aag aaa-3'); the plasmid for L67P mutation (pcDNA3/LKB1 L67Pmyc), LK L67P primer (SEQ ID NO: 47/5'-gtg aag gag gtg ccg gac tcg gag acg-3'); plasmid DNA for K781 mutation (pcDNA3/LKB1 K781myc), LK KI1 primer (SEQ ID NO: 48/5'-agg agg gcc gtc atc atc ctc aag aag-3') The DNA strand was newly synthesized by annealing the single-stranded template DNA of the plasmid with two primers; one was the primer for the introduction of the mutation, and the other was a selection primer (for bottom strand) appended to the kit. The prepared DNA was introduced into E. coli cells; clones resistant to the antibiotic, Gene Editor™, were selected to obtain the cells containing the plasmids with the mutation. The plasmids, which were verified to have the mutation by sequencing, were used for expression experiments.

The C-terminal end of LKB1 protein can be tagged with an epitope peptide (SEQ ID NO: 44/NH$_2$-YPYDVPDYASL-COOH) recognized by anti-HA antibody or tagged with a sequence of consecutive 6 histidine (H) residues (histidine hexamer), by introducing, into a variety of vectors, the DNA fragments prepared by PCR using LK E4 primer (SEQ ID NO: 42/5'-gat ggg ccc tta cag gga ggc ata gtc agg cac atc ata tgg gta ctg ctg ctt gca ggc cga-3') or LK E5 primer (SEQ ID NO: 43/5'-gat gaa ttc tta gtg atg gtg atg gtg atg ctg ctt gca ggc cga-3'), respectively, instead of LK E2 primer. By utilizing the tagged constructions, LKB1 protein can be detected by the methods using with anti-HA antibody or anti-histidine hexamer-antibody, or can be purified by an affinity-purification method with anti-HA antibody or the nickel column.

EXAMPLE 7

Gene Expression of LKB1 in Mammalian Cell and the Kinase Activity Assay

About 10 μg of the expression plasmid DNAs, including the plasmid DNA prepared for LKB1 expression (pcDNA3/LKB1myc), was introduced into COS7 cells (by transfection) by the method using SuperFect (Qiagen). Specifically, after about 10$^6$ COS7 cells were placed in a 10 cm dish and cultured overnight, a mixture consisting of 10 μg of plasmid DNA and 60 μl of SuperFect was added thereto and then cultured for about 3 hours. Subsequently, the cells were further cultured in a fresh medium for 1 to 2 days, and then harvested by using a trypsin-EDTA solution. The cells were suspended in an NP40 kinase lysis buffer (10 mM Tris-hydrochloride (pH7.8), 1% NP40, 0.15M sodium chloride, 1 mM EDTA, 50 mM sodium fluoride, 5 mM sodium pyrophosphate, 10 μg/ml aprotinin, and 1 mM PMSF); the proteins were solubilized by stirring the suspension at 4° C. for 30 minutes. Protein A/G plus agarose (Santa Cruz) was added to the cell lysate obtained, and the mixture was stirred for 30 minutes to remove non-specific proteins adsorbed by the beads. Anti-c-Myc antibody A14 (Santa Cruz) was added to the mixture and then the mixture was left to stand at 4° C. for 1 hour; protein A/G plus agarose (Santa Cruz) was added thereto, and the mixture was allowed to stand for another 1 hour. The resultant immune-complex was precipitated from the mixture by centrifugation, washed several times with the NP40 kinase lysis buffer, a buffer containing 1M sodium chloride and a solution of 50 mM Tris-hydrochloride (pH7.8); the precipitate was used to assay the kinase activity.

The kinase assay was performed in the reaction system of a 50 μl solution containing 50 mM Tris-hydrochloride (pH7.8), 1 mM DTT, 10 mM divalent cation (Mn, etc.), and 10 μCi of [γ-$^{32}$P] ATP. The immunoprecipitate was incubated in the kinase assay solution at 37° C. for 30 minutes and then the reaction was stopped by adding the SDS-PAGE sample buffer and boiling; the sample was subjected to SDS-PAGE. The gel was fixed with a methanol/acetic acid solution, dried and then analyzed by a BAS200 image-analyzer (Fuji Film). The kinase activity of LKB1 assayed was evaluated as the autophosphorylation activity. The protein expressed was detected by SDS-PAGE followed by Western blotting using anti-c-Myc antibody A14.

Figure 6:
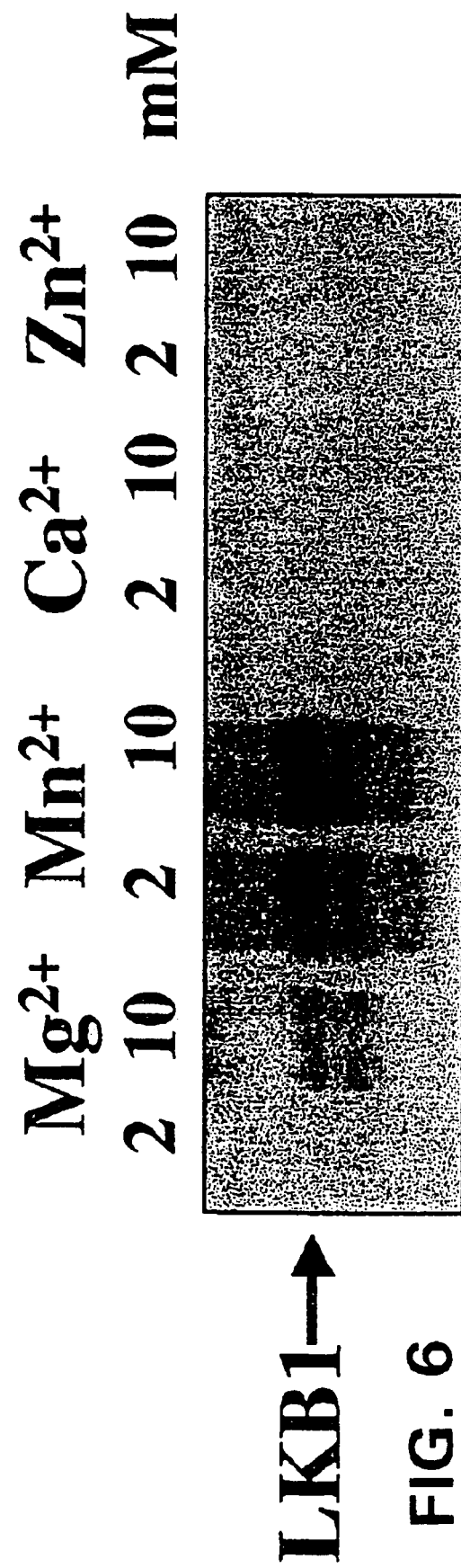
FIG. 6 shows the autophosphorylation activity of LKB1 protein investigated in the presence of various divalent cations; the protein was immunoprecipitated. The result shows that the autophosphorylation activity of LKB1 (kinase activity) is hardly enhanced by $Mg^{2+}$ but strongly enhanced by $Mn^{2+}$.
Figure 7:
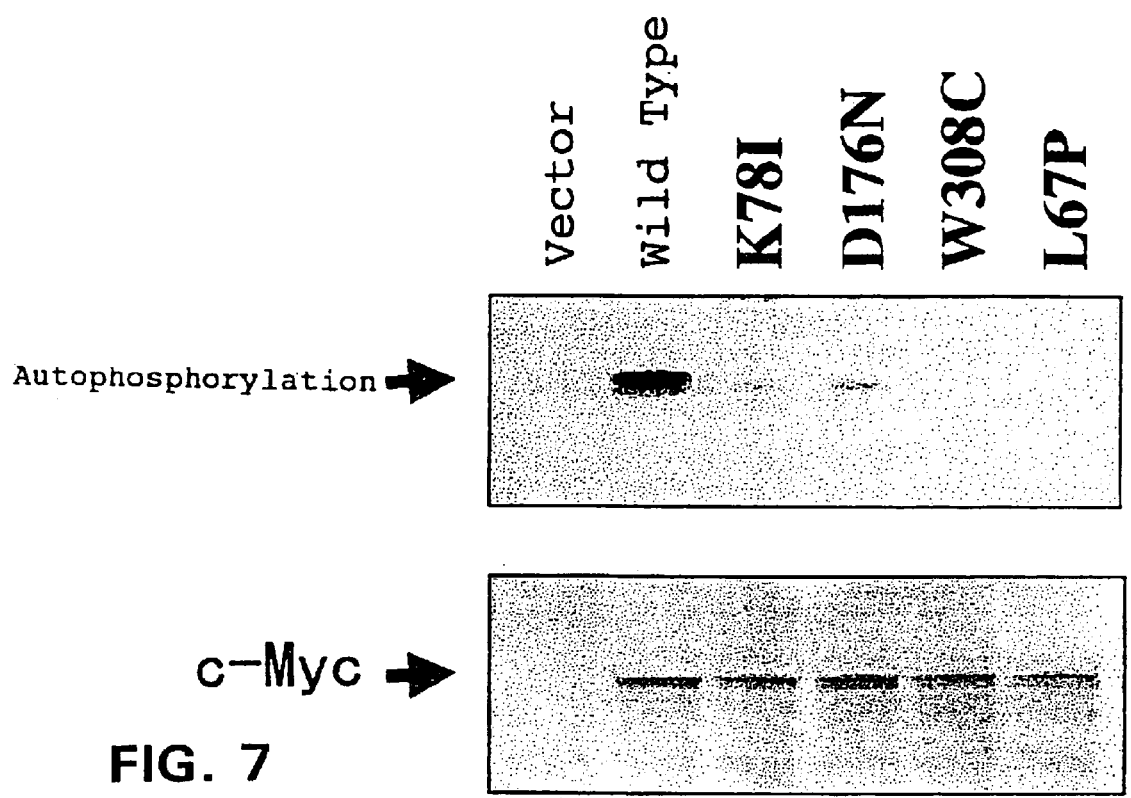
FIG. 7 shows the autophosphorylation activities of the wild-type LKB1 protein and the various mutants thereof. The top panel displays the autoradiography pattern showing autophosphorylation activity diagnosed by autoradiography; the bottom shows the results of a Western blotting stained with an anti-c-Myc antibody. Each protein is observed to be to be produced at a similar level.

The divalent cation-dependency in the kinase activity was first diagnosed, and the result showed that the kinase activity was hardly enhanced by $Mg^{2+}$ but enhanced intensely by $Mn^{2+}$ (FIG. 6). The kinase activity was diagnosed in the mutant proteins containing amino acids substituted in the Peutz-Jeghers patients; none of the mutant proteins exhibited the kinase activity (FIG. 7). These findings strongly suggest that LKB1 kinase loses its activity in Peutz-Jeghers patients and which becomes the cause of the disease.

EXAMPLE 8

Expression of LKB1 Protein in *E. coli*

Figure 8:
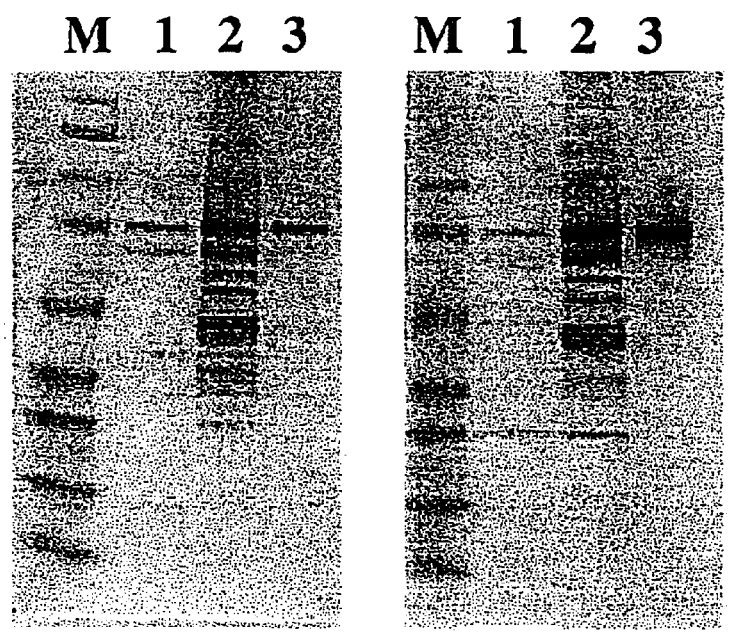
FIG. 8 shows an electrophoretic pattern of a GST-fusion of LKB1-myc protein expressed in *E. coli*, which was analyzed by Western blotting. M indicates the molecular weight marker; 1, a lysate of the *E. coli* cells prior to the induction by IPTG; 2, a lysate of the *E. coli* cells after the induction by IPTG; 3, the GST-fusion of LKB1-myc protein purified with glutathione Sepharose. The filter labeled with "Anti-Myc antibody" was stained using the anti-myc antibody; the one labeled with "Anti-LKB1 antibody" was stained with an affinity-purified anti-LKB1 peptide antibody.

Plasmid pGEX/LKB1myc was introduced into *E. coli* strain DH5 α, and a single-colony was selected. The *E. coli* cells were cultured in 10 ml of 2xYT medium at 37° C. overnight; an aliquot taken from the culture was diluted 100 times by fresh 2xYT medium; the *E. coli* cells were further cultured at 37° C. until the OD value of the medium measured at 600 nm reached 0.6. IPTG (isopropylβ-D (−)-thiogalactopyranoside) was then added to the culture at a final concentration of 0.1 mM, and the culture was prolonged for another several hours. The bacterial cells were collected by centrifugation, suspended in PBS containing 1% TritonX-100 and 1% Tween 20 and lysed by sonication to solubilize their proteins. LKB1 protein expressed as a fusion protein with glutathione-S-transferase (GST) was purified from the solubilized sample by an affinity purification method using glutathione Sepharose 4B (Pharmacia). The LKB1 protein expressed in *E. coli* was also detectable by Western blotting using anti-c-Myc antibody A14 (FIG. 8).

EXAMPLE 9

Preparation of Antibody Against LKB1 Protein and the use thereof

Two peptides were synthesized (Sawady Technology) based on the amino acid sequences of the N-terminal end and the C-terminal end of LKB1 protein, and the sequences are as follows: $NH_2$-CHRIDSTEVIYQPRRKRAKL-COOH (SEQ ID NO: 34) of LKB1 P6 peptide (amino acid 27–45) and $NH_2$-CLSTKSRAEGRAPNPARKA-COOH (SEQ ID NO: 31) of LKB1 P3 peptide (amino acid 400–417). The respective peptides were conjugated at the N-terminal cysteine with keyhole limpet hemocyanin (KLH) by a method using m-maleimidebenzoyl-N-hydroxysuccinimide ester (MBS) (Sawady Technology). The conjugated peptides were given to rabbits several times as antigens for immunization. The specific antibodies reacting to these peptides were purified from the antiserum by affinity columns prepared using cellulofine (Seikagaku Co.) to which the peptides were linked.

Figure 9:
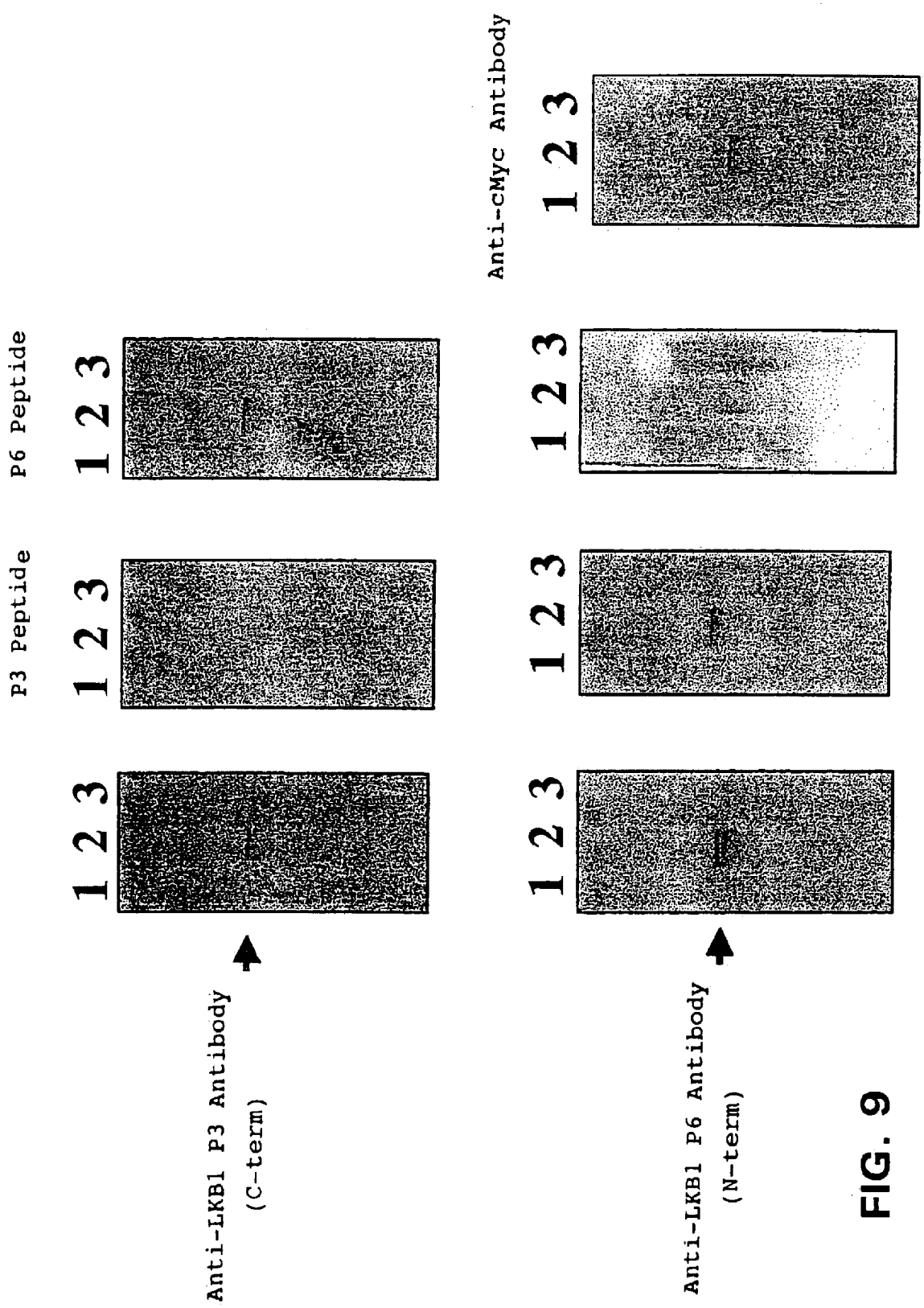
FIG. 9 shows the result of Western blotting using the respective antibodies. Lane 1 contains a sample lysate from COS7 cells with transfected DNA of pcDNA3 vector alone; lane 2, a lysate from COS7 cells with transfected pcDNA3/LKB1myc; lane 3, a lysate from HeLa S3 cells. The samples were stained with the antibodies indicated at the left and the anti-c-Myc antibody. Peptides used in the pre-incubation treatment are shown on the top.

The results of Western blotting with these antibodies (anti-LKB1P6 antibody and anti-LKB1P3 antibody recognize the N-terminal and C-terminal ends of LKB1 protein, respectively) are shown in FIG. 9. The results showed that the band (indicated by arrow) of about 55 kDa corresponding to the LKB1 protein expressed in COS7 cells was detectable by each antibody. Because the positive immunoreaction was blocked when the antibody was pre-incubated with a large excess of the corresponding peptide antigen, the reaction was considered to be specific to the epitope. In addition, no cross-reaction was seen with the lysate from HeLa S3 cells; the cells express no LKB1 protein; and thus it is safe to conclude that LKB1 protein can be detected with high specificity by these antibodies. It was also shown that the LKB1 protein expressed as a GST fusion protein in *E. coli* was detectable with anti-LKB1 P3 antibody (FIG. 8).

Figure 10:
FIG. 10 shows a tissue section of human fetal colon stained using anti-LKB1 P3 antibody. The cytoplasm of the epithelial cells is positive in the stain. The cells, which are assumed to be endocrine cells, are also stained very intensely.
Figure 11:
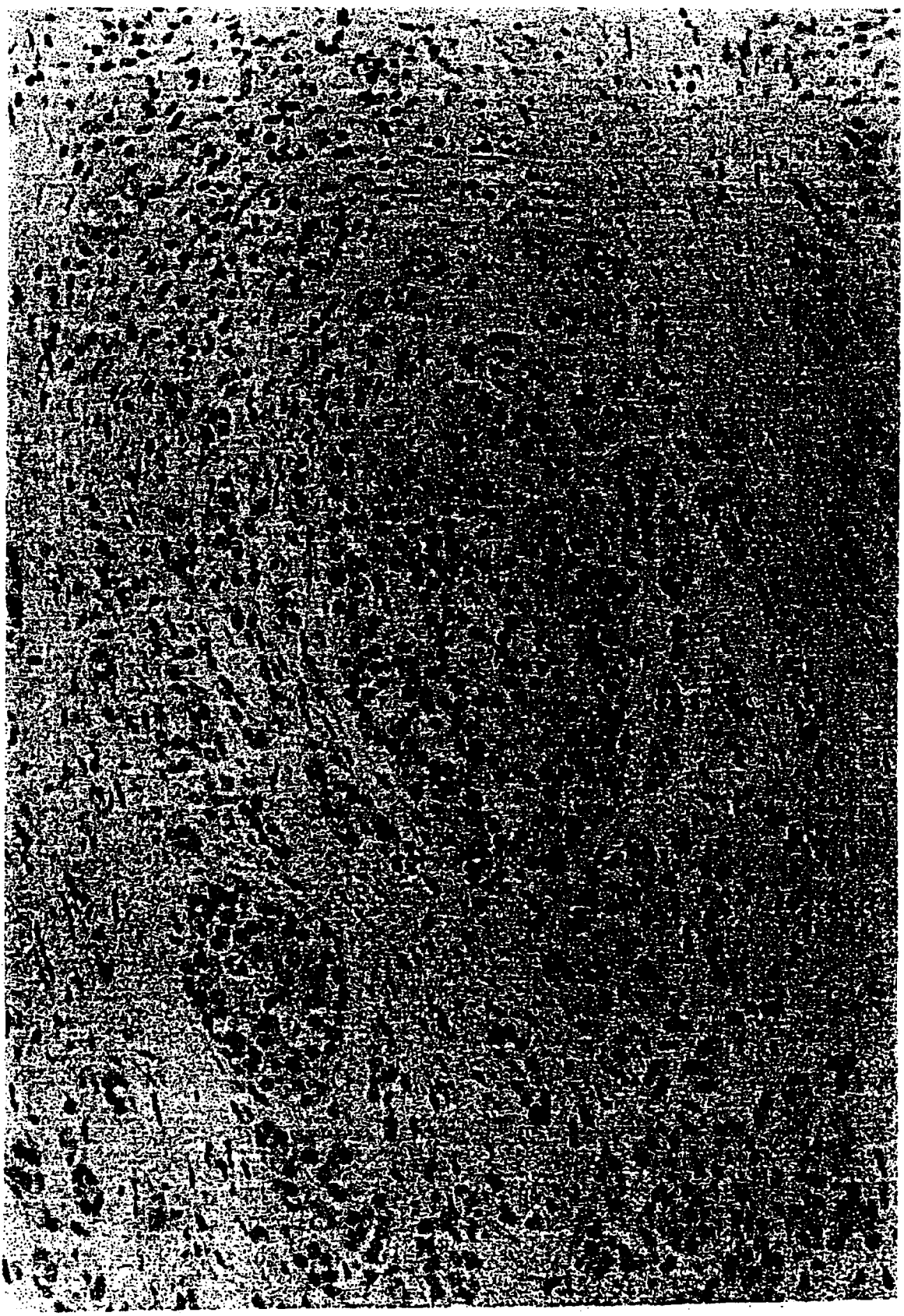
FIG. 11 shows a tissue section of human adult pancreas stained with the anti-LKB1 P3 antibody. The islet cells are positive in this staining.
Figure 12:
FIG. 12 shows a tissue section of human fetal testis stained with the anti-LKB1 P3 antibody. The undeveloped germ cells were stained intensely.

The results of immuno-staining of human tissue sections with the antibodies are shown in FIGS. 10, 11, and 12. FIG. 10 shows an immuno-stained tissue section of human fetal colon. The cytoplasm of the epithelial cells was positively stained. The cells, which are assumed to be endocrine cells, are also stained very intensely. FIG. 11 shows an immuno-stained tissue section of human adult pancreas. The islet cells are stained positively. FIG. 12 shows an immuno-stained tissue section of human fetal testis. The undeveloped germ cells are stained intensely. The immuno-staining patterns shown were obtained with anti-LKB1 P3 antibody; similar results were also obtained with anti-LKB1 P6 antibody. The positive immunoreactions shown were blocked when the antibody was pre-incubated with the corresponding peptide antigen, so that the staining was considered to be specific.

Industrial Applicability

The present invention revealed that Peutz-Jeghers syndrome was caused by the mutations in the LKB1 gene. The invention made it possible to diagnose and treat the diseases caused by the mutations in the LKB1 gene, such as Peutz-Jeghers syndrome, by utilizing the LKB1 gene, primers or probes designed based on the sequence thereof, LKB1 protein and the antibodies thereto.

What is claimed is:

1. A method of diagnosing Peutz-Jeghers syndrome, the method comprising the step of detecting one or more mutations in an LKB1 gene of an individual using a probe or primer comprising at least 15 contiguous nucleotides of any one of SEQ ID NOs: 1 to 4 or any one of the complements of SEQ ID NOs: 1 to 4, wherein detection of the mutation indicates that the individual has Peutz-Jeghers syndrome.

2. The method of claim 1, wherein the step of detecting one or more mutations in the LKB1 gene comprises the steps of:
   (a) providing a DNA sample from the individual;
   (b) amplifying the DNA using a primer DNA comprising at least 15 contiguous nucleotides of any one of SEQ ID NOs: 1 to 4 or any one of the complements of SEQ ID NOs: 1 to 4;
   (c) cleaving the amplified DNA into first DNA fragments;
   (d) fractionating the first DNA fragments according to their size;
   (e) hybridizing a DNA probe comprising at least 15 contiguous nucleotides of any one of SEQ ID NO: 1 to 4 or any one of the complements of SEQ ID NOs: 1 to 4 with the fractionated first DNA fragments; and
   (f) comparing the size of the first DNA fragments to the size of second DNA fragments from a healthy control, wherein a difference in size between the first fragments and the second fragments indicates the presence of one or more mutations in the individual's LKB1 gene.

3. The method of claim 1, wherein the step of detecting one or more mutations in the LKB1 gene comprises the steps of:
   (a) providing a RNA sample from the individual;
   (b) fractionating the RNA in the sample by size;
   (c) hybridizing a DNA probe comprising at least 15 contiguous nucleotides of any one of SEQ ID NOs: 1 to 4 or any one of the complements of SEQ ID NOs: 1 to 4 with the fractionated RNA; and
   (d) comparing the size of the hybridized RNA thus detected to that from a healthy control, wherein a difference in size between the RNA from the control and the individual indicates the presence of one or more mutations in the individual's LKB1 gene.

4. The method of claim 1, wherein the step of detecting one or more mutations in the LKB1 gene comprises the steps of:
   (a) providing a DNA sample from the individual;
   (b) amplifying the DNA using a primer DNA comprising at least 15 contiguous nucleotides of any one of SEQ ID NOs: 1 to 4 or any one of the complements of SEQ ID NOs: 1 to 4;
   (c) separating the amplified DNA into single stranded DNA;
   (d) fractionating the single stranded DNA on a non-denaturing gel; and
   (e) comparing the mobility of the fractionated single stranded DNA to that from a healthy control, wherein a difference in mobility between the single stranded DNA from the control and the individual indicates the presence of one or more mutations in the individual's LKB1 gene.

5. The method of claim 1, wherein the step of detecting one or more mutations in the LKB1 gene comprises the steps of:
   (a) providing a DNA sample from the individual;
   (b) amplifying the DNA using a primer DNA comprising at least 15 contiguous nucleotides of any one of SEQ ID NOs: 1 to 4 or any one of the complements of SEQ ID NOs: 1 to 4;
   (c) fractionating the amplified DNA on a DNA denaturing gradient gel; and
   (d) comparing the mobility of the fractionated DNA on the gel to that from a healthy control, wherein a difference in mobility between the DNA from the control and the individual indicates the presence of one or more mutations in the patient's LKB1 gene.

6. The method according to claim 1, wherein the individual has Peutz-Jeghers syndrome.

7. The method of claim 1, wherein the one or more mutations result in a disruption of the kinase domain of the LKB1 protein.

8. The method of claim 1, wherein at least one of the one or more mutations is an inversion.

9. The method of claim 1, wherein at least one of the one or more mutations is a deletion.

10. The method of claim 1, wherein at least one of the one or more mutations is aberrant splicing.

11. The method of claim 1, wherein at least one of the one or more mutations is a point mutation.

12. The method of claim 1, wherein at least one of the one or more mutations is premature termination.

13. The method of claim 1, wherein at least one of the one or more mutations is a frameshift mutation.

* * * * *

UNITED STATES PATENT AND TRADEMARK OFFICE
CERTIFICATE OF CORRECTION

PATENT NO.   : 6,800,436 B1
DATED        : October 5, 2004
INVENTOR(S)  : Dieter E. Jenne and Jun-Ichi Nezu It is certified that error appears in the above-identified patent and that said Letters Patent is hereby corrected as shown below:

Drawings,
FIG. 3A, " 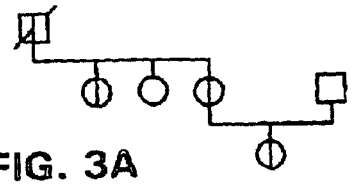 " should be replaced with the following:

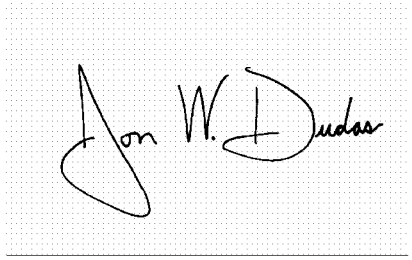

Column 57,
Line 22, after "any one of" change "SEQ ID NO:" to -- SEQ ID NOs: --.

Signed and Sealed this

Twenty-first Day of February, 2006

JON W. DUDAS
*Director of the United States Patent and Trademark Office*

SEQUENCE LISTING

<160> NUMBER OF SEQ ID NOS: 48

<210> SEQ ID NO 1
<211> LENGTH: 3765
<212> TYPE: DNA
<213> ORGANISM: Homo sapiens

<400> SEQUENCE: 1

| | | | | | | |
|---|---|---|---|---|---|---|
| gcccactgct | ttatgcggcc | gtttcatttg | atgtaatccg | agcccggtgc | gaagccgaag | 60 |
| caggtggatc | acctgaggtt | aggagttcgg | gaccagcctg | aacaatatgg | tgaaaccctg | 120 |
| tctctattga | aaatccaaaa | attatccagc | catggtggtg | tatgcctgta | gtcccagcta | 180 |
| ctccagaggc | tgagacagga | gaattgcttg | aatctgggaa | gcagaggttg | cagtgaacca | 240 |
| agatcatgcc | attgcactcc | agcccgggca | acagagcgag | actccgtctc | aaaaaaaaaa | 300 |
| aaagagagtc | agtgtggagg | gaagtgtctc | tgttgggtcc | gggtgctctg | tgggactctg | 360 |
| aggaaaagct | cgcaccaggt | agatgctgtt | ctgtccccat | gggtaaagga | caccccaaca | 420 |
| aaccgaggag | caaaatgtcc | tcgtatgccc | tcttcgcgca | gacctgccag | gaagagcaca | 480 |
| agaagaaaca | cccggactct | tctgtcaatt | tcgtggaatt | ctccaagaag | tgtttggaga | 540 |
| gatggaagac | cacgtctgca | aaggagaagt | gaagtttgaa | gagaaggcaa | aaagtgacaa | 600 |
| agctcgctgt | gacagggaga | ttaaaaatta | cattcctccg | aaatgtaaga | aagggtaaga | 660 |
| aaggaaagaa | aaaggatcgc | aatgctccta | gaaggccacc | atctgccttc | ttcctgtttt | 720 |
| gctctgaaca | tcgcccaaag | atcaaaagtg | acacccagg | cctatttgtc | gtggaaactg | 780 |
| caaagaaact | gggtgaaatg | tggtctgggc | agtcagccaa | agataaacaa | ccatatgagc | 840 |
| agaaagcagt | taagctacag | gagagatatg | aaaagggtat | tgctgcatat | cgtgctaagg | 900 |
| gcaaaagtga | agcaggaaag | aagggctcaa | agaagaacaa | accagaagat | gaggaggagg | 960 |
| aggaggagaa | agaagatgaa | gatgaggagg | aagagggtga | agatgaagaa | taaatggcta | 1020 |
| tcctttaatg | atgcctgtgc | agtgggcttg | ttttgctaag | aatgtgaatt | ctagtacagc | 1080 |
| tcagtattag | cttcagtata | aaactgtaca | aattttcgta | tagctcataa | gattctctgt | 1140 |
| acagaaaata | ctttttcttt | cttttctttt | ttttgagaca | gagtttcgct | cttgttgcct | 1200 |
| aggctggagt | gcaatggcgt | gatctcggct | caccgcaacc | tccgcctccc | gggtcctggt | 1260 |
| tcaagcagtt | ctcctgcctc | agcctcctga | gtagctggga | ttacaggcac | atgccaccac | 1320 |
| gctcagctaa | tttttgtatt | tttagtagag | atggggtttc | accatgttgg | ccaggctgct | 1380 |
| ttcaaactcc | tgacctcgtg | atccgcctgc | ttcggcctcc | caaaatactg | ggattacagg | 1440 |
| tgtgagccac | cgcaccctgc | ctaatgtccc | taaatattta | atggttttta | aaaaatttat | 1500 |
| tgtgtatggc | agcacagcac | acttgtagga | attagtatca | acagtacatc | ttgcgttttt | 1560 |
| taagatgctg | catttttaa | cattttgtaa | taaaattatg | cgtatcaaaa | aaacaaagaa | 1620 |
| attccgtgtg | tagttcacac | tcacagcaca | tctccgtcca | ggcacttgag | agaatgacta | 1680 |
| ggagggttc | ttggaggagg | tggtctttga | acggagaatc | catcttcaag | gattctgtct | 1740 |
| gtaatggtca | ccaagtattt | cctgagtcac | ttccatgtgt | cctgcagttc | tctgaagggg | 1800 |
| cgtgggacct | accgatgcca | attatccagc | attatctcca | gattccaaga | agttgggtg | 1860 |
| tgagccagca | atcagtacag | aaaagagata | ccaaaataag | tttgagttgg | ggagtgttcc | 1920 |
| ttcaacttca | gttttctgga | agagatcttt | tttttttttt | tgagacagag | tttcgctctt | 1980 |
| attgcccaag | ctggagtgca | gtggcacgat | ctcggctcac | cgcaacctcc | tcctcccggg | 2040 |

-continued

```
ttcaagcgat tctcctccct cagccttctg agtagctggg attacagaca tgcacctgta    2100
atttctacta aaaatacaaa aattagccgg gcgtggtggc gcacgcctgt aatctcagct    2160 actgggagg ctgaggcagg agaatcgctt gaaaccagga ggcggagatt gtaccaagat    2220
agtttgttcc agctaaacaa cctggcgcta gtgcaggaaa aggtggaagg cacgggcta    2280 gcacaggagg gttcaatatt ttcaacctta tcaagccata ttttggcaac tcttgttttt    2340
cacgagaagc ccccgctggg cttgtcccag cgctgtcctg aggcttcccc catgagttcc    2400 gataggcag aggccgccct gagcgtttct cttcccctg gtccaagagt ggctcaaaag     2460
aaggattttt gactggaatt ggccactttg tgttactttt tgacccttga cctcgcccca    2520 aaggggatg cggggaggg gctctggtag gggtggcccc gctccttcca ggtccgcaag     2580
cccaggttcc cgcccaccgg gctcagccca ccctgcggcc gttcagggag gccgttggca    2640
cccgtgacct acgaccccct tcccgagccc caccgaggtc acagccgtgg cctcgtctcc    2700
ccatgcctgc ttcccgcccc ctgcccgtga cgggcgtctc cgaggaccaa tgagcgcgct    2760
gtatccaccc ctcgggcggg gccaagcgcc gaccaatcgc cgctcgggcg cccggccggg    2820
tccaaacgct ccaatcgtca gcggcggcgg ggcgggcaga gggccgggga tggcaggttc    2880
aaccaacggg tgggcacgtc gtcctcgcga ggaggcgtgc cctgcggccg ggcgtgcggt    2940
gtccgcggcg gcgcagggag ggggagggag gtaaacaaga tggcggcggc gtgtcgggcg    3000
cggaaggggg aggcggcccg gggcgcccgc gagtgaggcg cggggcggcg aagggagcgc    3060
gggtggcggc acttgctgcc gcggccttgg atgggctggg ccccctcgc cgctccgcct    3120 cctccacacg cgcggcggcc gcggcgaggg ggacgcgccg ccccggggccc ggcaccttcg    3180 ggaaccccc ggcccggagc ctgcggcctg cgccgcctcg gccgccggga gccccgtgga    3240 gccccgccg ccgcgccgcc ccgcggaccg gacgctgagg gcactcgggg cggggcgcgc     3300
gctcgggcag acgtttgcgg ggaggggggc gcctgccggg ccccggcgac caccttgggg    3360 gtcgcggcc ggctcggggg gcgcccagtg cgggccctcg cgggcgccgg gcagcgacca     3420
gccctgagcg gagctgttgg ccgcggcggg aggcctcccg gacgccccca gcccccgaa    3480 cgctcgcccg ggccggcggg agtcggcgcc ccccgggagg tccgctcggt cgtccgcggc    3540
ggagcgtttg ctcctgggac aggcggtggg accggggcgt cgccggagac gcccccagcg    3600
aagttgggct ctccaggtgt gggggtcccg ggggtagcg acgtcgcgga cccggcctgt    3660
gggatgggcg gcccggagaa gactgcgctc ggccgtgttc atacttgtcc gtgggcctga    3720
ggtccccgga ggatgaccta gcactgaaaa gccccggccg cctc                     3765
```

<210> SEQ ID NO 2
<211> LENGTH: 1006
<212> TYPE: DNA
<213> ORGANISM: Homo sapiens
<220> FEATURE:
<221> NAME/KEY: exon
<222> LOCATION: (1)..(628)
<221> NAME/KEY: intron
<222> LOCATION: (629)..(1006)

<400> SEQUENCE: 2

```
cccagggtcc ccgaggacga agttgaccct gaccgggccg tctcccagtt ctgaggcccg     60
ggtcccactg gaactcgcgt ctgagccgcc gtccggacc cccggtgccc gccggtccgc    120
agaccctgca ccgggcttgg actcgcagcc gggactgacg tgtagaacaa tcgtttctgt    180
tggaagaagg gttttttccct tcctttggg gttttttgttg ccttttttttt ttctttttc     240 tttgtaaaat tttggagaag ggaagtcgga acacaaggaa ggaccgctca cccgcggact    300
```

```
cagggctggc ggcgggactc caggaccctg ggtccagc atg gag gtg gtg gac ccg     356
                                          Met Glu Val Val Asp Pro
                                          1               5 cag cag ctg ggc atg ttc acg gag ggc gag ctg atg tcg gtg ggt atg       404
Gln Gln Leu Gly Met Phe Thr Glu Gly Glu Leu Met Ser Val Gly Met
        10                  15                  20 gac acg ttc atc cac cgc atc gac tcc acc gag gtc atc tac cag ccg       452
Asp Thr Phe Ile His Arg Ile Asp Ser Thr Glu Val Ile Tyr Gln Pro
            25                  30                  35 cgc cgc aag cgg gcc aag ctc atc ggc aag tac ctg atg ggg gac ctg       500
Arg Arg Lys Arg Ala Lys Leu Ile Gly Lys Tyr Leu Met Gly Asp Leu
40                  45                  50 ctg ggg gaa ggc tct tac ggc aag gtg aag gag gtg ctg gac tcg gag       548
Leu Gly Glu Gly Ser Tyr Gly Lys Val Lys Glu Val Leu Asp Ser Glu
55              60                  65                  70 acg ctg tgc agg agg gcc gtc aag atc ctc aag aag aag aag ttg cga       596
Thr Leu Cys Arg Arg Ala Val Lys Ile Leu Lys Lys Lys Lys Leu Arg
                75                  80                  85 agg atc ccc aac ggg gag gcc aac gtg aag aa  gtaagtatggc ttgctggggt   649
Arg Ile Pro Asn Gly Glu Ala Asn Val Lys Lys
                90                  95 cggggccggg ccgggccagt cacggtgctg atggttctgt cttccttcct tctctcctcc     709
ctccctccct tacttcctct taacaccctg agctggaccc gtctggcgcc tgtgtcctcc     769
gtgccaggga gagcgtggtt gggggcctgc gttacggact tcactcagg caaggccagt      829 tgtcgcagcg gggcgtgcgt ttgcatgggc tcttggactc cagttaaaat gccctggtag     889
cgaaaccctc ctgagaaggg agcggccccc aatcccctaa gactagcccc ttggctcccc     949
cagctgtcca aggagcagag gcgcccagtg gaatcagcct gtgtttgttt gggcccc        1006
```

<210> SEQ ID NO 3
<211> LENGTH: 5661
<212> TYPE: DNA
<213> ORGANISM: Homo sapiens
<220> FEATURE:
<221> NAME/KEY: intron
<222> LOCATION: (1)..(456)
<221> NAME/KEY: exon
<222> LOCATION: (457)..(540)
<221> NAME/KEY: intron
<222> LOCATION: (541)..(1363)
<221> NAME/KEY: exon
<222> LOCATION: (1364)..(1453)
<221> NAME/KEY: intron
<222> LOCATION: (1454)..(2412)
<221> NAME/KEY: exon
<222> LOCATION: (2413)..(2545)
<221> NAME/KEY: intron
<222> LOCATION: (2546)..(2620)
<221> NAME/KEY: exon
<222> LOCATION: (2621)..(2757)
<221> NAME/KEY: intron
<222> LOCATION: (2758)..(3252)
<221> NAME/KEY: exon
<222> LOCATION: (3253)..(3380)
<221> NAME/KEY: intron
<222> LOCATION: (3381)..(3988)
<221> NAME/KEY: exon
<222> LOCATION: (3989)..(4046)
<221> NAME/KEY: intron
<222> LOCATION: (4047)..(5024)
<221> NAME/KEY: exon
<222> LOCATION: (5025)..(5212)
<221> NAME/KEY: intron
<222> LOCATION: (5213)..(5661)

<400> SEQUENCE: 3

```
ggtgaaaccc tgtctgtact aaaatacaaa aaaattagcc ggctgtggtg acacgtgcct    60
gtagtcccag ctactcggga ggctgaggca gggaaatcac ttgaacctgg gaggcagagg   120
ttgcagtgag ctgagatcgg gccaccgtgc tccagcctag gacagagca agactctgtc    180 tcagaaaaaa aaaaaagtgt cctaactgtg tcctccaaag ccctcgccgg ccgatgacag   240
actagagggc gctgtgctcc accccctac cgccctgagc ctggacgcgt ggcccctgca    300
gggccctttc ccacagcact gtgaactcac agcttctctc tagggaaggg aggagtacg    360 ccacttccac agggagatgg ggaggccgac tccagggatc caggccatca tcctgacgtt   420
gggtcggctg ataccccct gtcctctctg tcccag g gaa att caa cta ctg agg    475
                                        Glu Ile Gln Leu Leu Arg
                                                              100 agg tta cgg cac aaa aat gtc atc cag ctg gtg gat gtg tta tac aac     523
Arg Leu Arg His Lys Asn Val Ile Gln Leu Val Asp Val Leu Tyr Asn
    105                 110                 115 gaa gag aag cag aaa at  atatccttttcc ggtgttggga ccgcggggcc          571
Glu Glu Lys Gln Lys Met
120                 125 tccgtgggag gggctggggc cctgggtccg cctgcctcga ggcctgctcc tcttcccgtc   631
tccttgaagg agactggcac acgagggccg tggccttccc tggttccccg gaagtcagcc   691
attgtggcaa tggctgcgca gcttgctgaa aggggccctg agccctggcc cctgtgtctt   751
gggcccgtgg ggtgtcaagt cccttttttc tcagagtctc ctcccaggct aaccagggt    811 gtagccacgg tctgcctgag acaggccacg cgggctgacc gttgtgggcc attttggtcg   871
tggctgggcg tgtcctcgtg tcatctgtgg acacccccat gggtcttacg ggcacagcct   931
ccctacgggg actttgcttc ctaaggccct gtcccagag caagagccag aagtggtcct    991
gaggctgggg ctgtgttccc tgagccacgc ggtcaggggc cctgggaccg tcctgcatgg  1051
gcccgagcct gcttgggggg gcgtccagga ggcaccatcc cccgcccatg gcagggtgg   1111 gggacgtgag ccccgcagga acgctgcccc aagagtcagc cctgtcctcc ccttcccgt   1171 aggctccttc ctcctgggac gctggggccc ctgggccttt tcagaggggt ggctgagggc  1231
agggtgggcc ctggtcccga ggaggggcaa ggtgggtgca gagggtccct ccagagcccc  1291 tttctggcc cccgtgctcc ctgggcctgt gagtggggcc gcccctgag ctgtgtgtcc    1351 ttagcgcccc ac g tat atg gtg atg gag tac tgc gtg tgt ggc atg cag   1400
             Tyr Met Val Met Glu Tyr Cys Val Cys Gly Met Gln
                         130                 135 gaa atg ctg gac agc gtg ccg gag aag cgt ttc cca gtg tgc cag gcc    1448
Glu Met Leu Asp Ser Val Pro Glu Lys Arg Phe Pro Val Cys Gln Ala
    140                 145                 150 cac gg  gtgcgtgcgcg gggcagggc caggtgggg cggggccgg gggccaggca      1504
His Gly
    155 gggcaggctc ctttccgtga ggccacactg cttgtcctga tattcattga catgaaggcc  1564 caagtttttt tgtttttttg tttttttgtg ttttttttcg agatggagtc tcactctgtc  1624 gcccaggctg gagtgcaatg gtgcgatctc ggctcactgc aagctccgcc tcgaggttc   1684 acgccattct tctgcctcag cttcccgagt agctgggatt acaggcgccc gccaccacgc  1744 ccggctaatt ttttgtattt ttagtagaga cggggtttca ccgtgttagc caggatggtc  1804 tcaaactcct gacctcgtga tccgcctgcc tcagcctccc aaagtgctgg gattacaggc  1864 atgagctacc acgccggcc ttgtaaaggc ccaagttttt aaaaacagtt ttgggggtccc  1924 ccatgtgtgg catccacagg cagggctgct gccaaccctc cgcctccatc tttgctgggc  1984
```

-continued

```
ctgctgcctg aggccagtgg cctgcttcca gcccatcgct ggcagccgcc tgccctgacc    2044
agatctcctg gatgcaggtc tgtggcctca gagtcagggc cccttgctgc tgcaggacca    2104
caggggcagg gaggggcctg ctgttccagc aagactttgg ggtgcagccg gcctgtggcc    2164
cacaggaaaa tgagacctgt ggacatccgg ggccctgcca gacgtggctc ggccggacga    2224
gggtggccac tgcaggcgca ggtgtggctc cctgctggac ctagcctttc tctgtcctg     2284 tgtgcctgga cttctgtgac ttcccagctg ggcctgtggt gtttgggagg ctcccaggca    2344
gctgcaaagg ggaccctgt gagggcagg gaggcctcgg ccccaggacg ggtgtgtgct     2404 gcccgcag g tac ttc tgt cag ctg att gac ggc ctg gag tac ctg cat       2452
          Tyr Phe Cys Gln Leu Ile Asp Gly Leu Glu Tyr Leu His
              160                 165 agc cag ggc att gtg cac aag gac atc aag ccg ggg aac ctg ctg ctc      2500
Ser Gln Gly Ile Val His Lys Asp Ile Lys Pro Gly Asn Leu Leu Leu
    170                 175                 180 acc acc ggt ggc acc ctc aaa atc tcc gac ctg ggc gtg gcc gag          2545
Thr Thr Gly Gly Thr Leu Lys Ile Ser Asp Leu Gly Val Ala Glu
185                 190                 195 gtaggcacgt gctaggggg gcccctgggc gccccctccc gggcactccc tgagggctgc     2605
acggcaccgc cacag gca ctg cac ccg ttc gcg gcg gac gac acc tgc cgg     2656
                  Ala Leu His Pro Phe Ala Ala Asp Asp Thr Cys Arg
                      200             205                 210 acc agc cag ggc tcc ccg gct ttc cag ccg ccc gag att gcc aac ggc      2704
Thr Ser Gln Gly Ser Pro Ala Phe Gln Pro Pro Glu Ile Ala Asn Gly
    215                 220                 225 ctg gac acc ttc tcc ggc ttc aag gtg gac atc tgg tcg gct ggg gtc      2752
Leu Asp Thr Phe Ser Gly Phe Lys Val Asp Ile Trp Ser Ala Gly Val
    230                 235                 240 acc ct  gtaagtgcccc gcccccccgg gcactcacca cacgcacact ccgagggggcc     2808
Thr Leu
    245 tctgcgtctt gggcagctgc cggcctgtgg gcgcagggcg tggccaccgg cccagaccct    2868 ctctggccac agccgctagg gggtgcttac tttatggaaa tgtaactcat acggcagatg    2928 gtggttcacc cgtgtgaagt gcagcctggc ccgtcaggga tcttcacaga gtggcacggc    2988 cgaccctcct cccagagccc cacagggaag ctgggcgggt gacagcagct ccaggcccct    3048 tccccgggtg gtccagagg acactcccct cctaccccgt agcctccact agtggaaggt     3108 ggtgaagaca gaggtgtcct tgagtccaca gggcctctgg tccagcagcc acgggacgcc    3168 tctgtccctg gggtagagct ggggctccta ggcgtcaac caccttgact gaccacgcct     3228 ttcttccctc ccctcgaaat gaag c tac aac atc acc acg ggt ctg tac ccc     3280
                              Tyr Asn Ile Thr Thr Gly Leu Tyr Pro
                                                      250 ttc gaa ggg gac aac atc tac aag ttg ttt gag aac atc ggg aag ggg      3328
Phe Glu Gly Asp Asn Ile Tyr Lys Leu Phe Glu Asn Ile Gly Lys Gly
255                 260                 265                 270 agc tac gcc atc ccg ggc gac tgt ggc ccc ccg ctc tct gac ctg ctg      3376
Ser Tyr Ala Ile Pro Gly Asp Cys Gly Pro Pro Leu Ser Asp Leu Leu
                275                 280                 285 aaa g gtgggagcctca tccctctgcc cgcagcccca gggaggcggg gcttttgtgc       3432
Lys agaaatgtag ggttgggggt gtcaggtggg gggctattgg ccccgagacc ccagcaggca    3492
ttgagaggac tgagtggaga ggccgacctc cccgcagggc ctggtttgcc aggtccctca    3552
gctccaccct gcttctgggc cctgttcacc ctccgaactc ccaccccaga gggcagtgct    3612
gccctgcgcc tcccccagcc ccaccctcgg gggctccctg gcttgcaggg tctgtcaggg    3672
```

```
                                                              -continued ttgtcctgct gcacttccta cgcatggcag caggtggcac tggccgtccg tccatctgcc    3732
cagtggcctt gggagaacgg aaccgccctg ccgtccagc ccagccctgt ctccctgcca    3792
gccgcgcaca ggctgtcccc ggcatgtccc aggagtggag tggcctctgt cagggagacc    3852
gcctgtgcgc ggggtccccc ttaggagcgt ccaggtatca cccagggcct gacaacagag    3912
gctgggcagg cggggacggt tggtggggtc tcaggcctgt gcccagctga caggctcctc    3972
gccggcttct cctcag gg atg ctt gag tac gaa ccg gcc aag agg ttc tcc    4023
                 Gly Met Leu Glu Tyr Glu Pro Ala Lys Arg Phe Ser
                                  290                 295 atc cgg cag atc cgg cag cac ag gtgagcggccc ctgggggcag tggggccgag    4077
Ile Arg Gln Ile Arg Gln His Ser
300                 305 gctgcaggga ggccggccat gtgggcagct ggttgagcgg gcgctagagc agggcgtggt    4137
gggggtgcca ggctgggctg gggccagacc ccgtgcagcg cccgcagttc tcggggcccg    4197 agtgggtct ctgggcagtg tcctgttacc ggccagaccc aggcgccttg tccgaactgg    4257
ggtctgagtg aggacatgcg tccgtccctg ccctaggcat ggagatgcgc caggaagggc    4317
acagctggtc ccaaacactg gcgagagcct ctctttttcc cctcctcctg gggctcccag    4377
cagcagggtg tggctgggat ccagcccagg gcccccagct ccatgacagg gaagacagag    4437
cagcggacgg ggtcagcagg ccccacagtg ccgcctccct cacttcgtgg gctctgctcc    4497
tctgcaccag ccctggagg cccttgagcc gtctgctgga gccctccga gccccgaggc    4557 cacccactga gaccggctct gggagtggga gtgtccggac ccctgaggcg ctggtgctga    4617
ttgtgccttg ggggtctctg cacagctcgg gtcatctggg cgcctggcgg ggactggggc    4677
tgccccccga tagcctcctg ggctgggatg tgctcagggc cccccagacc cccttctggc    4737 cttttgctggc tttgcagcca gcatccatct ggtgggtgct ggcttctgag tgccacctgg    4797
gacacaggcc tcagggtgga ggggacatct gtcaggcttg gagtcaggtc agcctgcctg    4857
ctcctagagg acatggctga gcttctgtgg tcacagccac ccttgcacg gcctggtccc    4917 agctcctgag tgtgtggcag gtaccctggg cccagaggag ctgggtcgga aaactggacc    4977
gccctggtgc cagcctgaca ggcgccactg cttctgggcg tttgcag c tgg ttc cgg    5034
                                                      Trp Phe Arg
                                                              310 aag aaa cat cct ccg gct gaa gca cca gtg ccc atc cca ccg agc cca    5082
Lys Lys His Pro Pro Ala Glu Ala Pro Val Pro Ile Pro Pro Ser Pro
                315                 320                 325 gac acc aag gac cgg tgg cgc agc atg act gtg gtg ccg tac ttg gag    5130
Asp Thr Lys Asp Arg Trp Arg Ser Met Thr Val Val Pro Tyr Leu Glu
        330                 335                 340 gac ctg cac ggc gcg gac gag gac gag gac ctc ttc gac atc gag gat    5178
Asp Leu His Gly Ala Asp Glu Asp Glu Asp Leu Phe Asp Ile Glu Asp
    345                 350                 355 gac atc atc tac act cag gac ttc acg gtg ccc g gtgagtctggcg         5224
Asp Ile Ile Tyr Thr Gln Asp Phe Thr Val Pro
360                 365 ggggcccctg cccggctctg ctgactcggc caggatgtcc cacgggagca gggtgcctgc    5284
ctgtctgcaa caaggacagc ttctgccctc tggtggccaa tcccacgtcc ccaaagcctc    5344
cagcccacct gcaggctgcc tccgcccgc gggccgctgg acatggctg aaaggtgtgg    5404 ggtcagcggg ggcaccagcc caggcctgtc tggccaggag ggttcctcag gcgtctctcc    5464
gggtgctgcc cagccaggca ccaccaccg gccttggcct gagtcccagc aggagcaggc    5524
gggggagccc cagggtcggg ggagggtagg tgagagtcag ggtgcagggt ggcccctcag    5584
```

```
acagctggca tgagagaggg tccagtggcc ctccctcccg tcgtccctga ggcctgcccg    5644
ctggccctga tgccggc                                                  5661
```

<210> SEQ ID NO 4
<211> LENGTH: 2095
<212> TYPE: DNA
<213> ORGANISM: Homo sapiens
<220> FEATURE:
<221> NAME/KEY: intron
<222> LOCATION: (1)..(454)
<221> NAME/KEY: exon
<222> LOCATION: (455)..(2095)

<400> SEQUENCE: 4

```
tttcgcgtgc ctggcctgag cctggcccga gcctggccct cctgtgtcct cacagatgag     60
catgtggcgg ctcctgggcc tctagaacca accatgggcc agggtgcccc aggggagcac    120
gggagggtcc tgccttgtca gcttgcctcc tactcgtgag gttcctgcag tcagtacctg    180
ggtggggtcc cacctgcggc catggcaggt gcaacagacg tggtggaggg gacactcctg    240
cccaggccat ctgcgggagg ctcagccccg gggggtgcct cccagagctg ctgggggca    300 gcatttcagg ctggatacac ctgggcctga cccgggggcg gcatggcct gggcagcagc    360 tgtaagtgcg tccccgtggt gggggccagc caggtccctg tggctctggg gttgcgcccc    420
tcagctcagg ccacacttgc cgtctccctc ccag  ga cag gtc cca gaa gag gag    474
                                      Gly Gln Val Pro Glu Glu Glu
                                                 370         375 gcc agt cac aat gga cag cgc cgg ggc ctc ccc aag gcc gtg tgt atg      522
Ala Ser His Asn Gly Gln Arg Arg Gly Leu Pro Lys Ala Val Cys Met
         380                 385                 390 aac ggc aca gag gcg gcg cag ctg agc acc aaa tcc agg gcg gag ggc      570
Asn Gly Thr Glu Ala Ala Gln Leu Ser Thr Lys Ser Arg Ala Glu Gly
     395                 400                 405 cgg gcc ccc aac cct gcc cgc aag gcc tgc tcc gcc agc agc aag atc      618
Arg Ala Pro Asn Pro Ala Arg Lys Ala Cys Ser Ala Ser Ser Lys Ile
 410                 415                 420 cgc cgg ctg tcg gcc tgc aag cag cag tgaggctggc cgcctgcagg             665
Arg Arg Leu Ser Ala Cys Lys Gln Gln
425                 430 tggggcgcgg cggggcccgg gtggggcatg tggggacaac gcctggatgc cacagccagc    725
cgtgagcata gcccgcgcta gtcagtcatg gtgaccgtca cgtggctgcg cgtggttgcc    785
atgtggcctt tgggtggctt ggccacgtag cgatccccgt ggagggtgcc gtctcggggc    845
ctggtgtctg gccagcgtgc tggtcatgga ggcctacgtg tggcggggct ctgggggggc    905
gtgccgtcct cacagccacc tctcagagtg ggtgcattcc gaggacctg ccctgggcct    965 ggcgcccct ccccatgccc gcgccgcttc caggaaaggc ttatgctggg ctcagcccag    1025
aggcttttga gcaccagtgg gtggtgggt gtggggaggg gccgcggcct ccatggctct    1085
gccggggtgc cgcaggctct gagccagctg ccaagtatgg ctgaggctga gtcgtgccgg    1145
acgctgccct gtctctccct gtgtgcctgc ctcctctccc agcccagcc ccagccccgg    1205 gtgggagacg gagtcccaga ggtgtcagag acccttaagt cacctgccga ggatgcgggg    1265
tggatggggg cccgaggctg aagccctgc cttgccacag cccctctccc aggttttggg    1325
ggccaccgcc tgagttacat gtctgtcccc caaatgggtg cccacagccc atccaccagc    1385
gtcagagccc gccaggcccc actgcaaaag gccacacaat gtaccccggg agtgactcaa    1445
gggtggcctt ccctggcctc ccctgctgcc ccccaggagt ccggtagccc catgactgta    1505
```

-continued

| | |
|---|---|
| cctcagcttc tccatcctcc caggggcccg cgggaggcgg agaaccggtg cccaggctga | 1565 |
| cctcttccgt cttccttcca ccctgcagcc cgtgtccagg agccccgcca ggtgcccgcg | 1625 |
| ccaggccctc agtcttcctg ccggttccgc ccgccctccc ggagaggtgg ccgccatgct | 1685 |
| tctgtgccga ccacgcccca ggacctccgg agcccctgc agggccgggc agggggacag | 1745 |
| cagggaccgg gcgcagccct cccccctcgg ccgcccggca gtgcacgcgg cttgttgact | 1805 |
| tcgcagcccc gggcggagcc ttcccgggcg ggcgtgggag gagggaggcg gcctccatgc | 1865 |
| actttatgtg gagactactg gccccgcccg tggcctcgtg ctccgcaggg cgcccagcgc | 1925 |
| cgtccggcgg ccccgccgca gaccagctgg cgggtgtgga gaccaggctc ctgaccccgc | 1985 |
| catgcatgca gcgccacctg gaagccgcgc ggccgctttg gttttttgtt tggttggttc | 2045 |
| cattttcttt ttttcttttt tttttaaga aaaataaaa ggtggatttg | 2095 |

<210> SEQ ID NO 5
<211> LENGTH: 1302
<212> TYPE: DNA
<213> ORGANISM: Homo sapiens
<220> FEATURE:
<221> NAME/KEY: CDS
<222> LOCATION: (1)..(1302)

<400> SEQUENCE: 5

| | |
|---|---|
| atg gag gtg gtg gac ccg cag cag ctg ggc atg ttc acg gag ggc gag<br>Met Glu Val Val Asp Pro Gln Gln Leu Gly Met Phe Thr Glu Gly Glu<br>1               5                   10                  15 | 48 |
| ctg atg tcg gtg ggt atg gac acg ttc atc cac cgc atc gac tcc acc<br>Leu Met Ser Val Gly Met Asp Thr Phe Ile His Arg Ile Asp Ser Thr<br>            20                  25                  30 | 96 |
| gag gtc atc tac cag ccg cgc cgc aag cgg gcc aag ctc atc ggc aag<br>Glu Val Ile Tyr Gln Pro Arg Arg Lys Arg Ala Lys Leu Ile Gly Lys<br>        35                  40                  45 | 144 |
| tac ctg atg ggg gac ctg ctg ggg gaa ggc tct tac ggc aag gtg aag<br>Tyr Leu Met Gly Asp Leu Leu Gly Glu Gly Ser Tyr Gly Lys Val Lys<br>    50                  55                  60 | 192 |
| gag gtg ctg gac tcg gag acg ctg tgc agg agg gcc gtc aag atc ctc<br>Glu Val Leu Asp Ser Glu Thr Leu Cys Arg Arg Ala Val Lys Ile Leu<br>65                  70                  75                  80 | 240 |
| aag aag aag aag ttg cga agg atc ccc aac ggg gag gcc aac gtg aag<br>Lys Lys Lys Lys Leu Arg Arg Ile Pro Asn Gly Glu Ala Asn Val Lys<br>                85                  90                  95 | 288 |
| aag gaa att caa cta ctg agg agg tta cgg cac aaa aat gtc atc cag<br>Lys Glu Ile Gln Leu Leu Arg Arg Leu Arg His Lys Asn Val Ile Gln<br>            100                 105                 110 | 336 |
| ctg gtg gat gtg tta tac aac gaa gag aag cag aaa atg tat atg gtg<br>Leu Val Asp Val Leu Tyr Asn Glu Glu Lys Gln Lys Met Tyr Met Val<br>        115                 120                 125 | 384 |
| atg gag tac tgc gtg tgt ggc atg cag gaa atg ctg gac agc gtg ccg<br>Met Glu Tyr Cys Val Cys Gly Met Gln Glu Met Leu Asp Ser Val Pro<br>    130                 135                 140 | 432 |
| gag aag cgt ttc cca gtg tgc cag gcc cac ggg tac ttc tgt cag ctg<br>Glu Lys Arg Phe Pro Val Cys Gln Ala His Gly Tyr Phe Cys Gln Leu<br>145                 150                 155                 160 | 480 |
| att gac ggc ctg gag tac ctg cat agc cag ggc att gtg cac aag gac<br>Ile Asp Gly Leu Glu Tyr Leu His Ser Gln Gly Ile Val His Lys Asp<br>                165                 170                 175 | 528 |
| atc aag ccg ggg aac ctg ctc ctc acc acc ggt ggc acc ctc aaa atc<br>Ile Lys Pro Gly Asn Leu Leu Leu Thr Thr Gly Gly Thr Leu Lys Ile<br>            180                 185                 190 | 576 |
| tcc gac ctg ggc gtg gcc gag gca ctg cac ccg ttc gcg gcg gac gac<br> | 624 |

```
Ser Asp Leu Gly Val Ala Glu Ala Leu His Pro Phe Ala Ala Asp Asp
            195                 200                 205 acc tgc cgg acc agc cag ggc tcc ccg gct ttc cag ccg ccc gag att      672
Thr Cys Arg Thr Ser Gln Gly Ser Pro Ala Phe Gln Pro Pro Glu Ile
210                 215                 220 gcc aac ggc ctg gac acc ttc tcc ggc ttc aag gtg gac atc tgg tcg      720
Ala Asn Gly Leu Asp Thr Phe Ser Gly Phe Lys Val Asp Ile Trp Ser
225                 230                 235                 240 gct ggg gtc acc ctc tac aac atc acc acg ggt ctg tac ccc ttc gaa      768
Ala Gly Val Thr Leu Tyr Asn Ile Thr Thr Gly Leu Tyr Pro Phe Glu
            245                 250                 255 ggg gac aac atc tac aag ttg ttt gag aac atc ggg aag ggg agc tac      816
Gly Asp Asn Ile Tyr Lys Leu Phe Glu Asn Ile Gly Lys Gly Ser Tyr
        260                 265                 270 gcc atc ccg ggc gac tgt ggc ccc ccg ctc tct gac ctg ctg aaa ggg      864
Ala Ile Pro Gly Asp Cys Gly Pro Pro Leu Ser Asp Leu Leu Lys Gly
    275                 280                 285 atg ctt gag tac gaa ccg gcc aag agg ttc tcc atc cgg cag atc cgg      912
Met Leu Glu Tyr Glu Pro Ala Lys Arg Phe Ser Ile Arg Gln Ile Arg
290                 295                 300 cag cac agc tgg ttc cgg aag aaa cat cct ccg gct gaa gca cca gtg      960
Gln His Ser Trp Phe Arg Lys Lys His Pro Pro Ala Glu Ala Pro Val
305                 310                 315                 320 ccc atc cca ccg agc cca gac acc aag gac cgg tgg cgc agc atg act    1008
Pro Ile Pro Pro Ser Pro Asp Thr Lys Asp Arg Trp Arg Ser Met Thr
            325                 330                 335 gtg gtg ccg tac ttg gag gac ctg cac ggc gcg gac gag gac gag gac    1056
Val Val Pro Tyr Leu Glu Asp Leu His Gly Ala Asp Glu Asp Glu Asp
        340                 345                 350 ctc ttc gac atc gag gat gac atc atc tac act cag gac ttc acg gtg    1104
Leu Phe Asp Ile Glu Asp Asp Ile Ile Tyr Thr Gln Asp Phe Thr Val
    355                 360                 365 ccc gga cag gtc cca gaa gag gag gcc agt cac aat gga cag cgc cgg    1152
Pro Gly Gln Val Pro Glu Glu Glu Ala Ser His Asn Gly Gln Arg Arg
370                 375                 380 ggc ctc ccc aag gcc gtg tgt atg aac ggc aca gag gcg gcg cag ctg    1200
Gly Leu Pro Lys Ala Val Cys Met Asn Gly Thr Glu Ala Ala Gln Leu
385                 390                 395                 400 agc acc aaa tcc agg gcg gag ggc cgg gcc ccc aac cct gcc cgc aag    1248
Ser Thr Lys Ser Arg Ala Glu Gly Arg Ala Pro Asn Pro Ala Arg Lys
            405                 410                 415 gcc tgc tcc gcc agc agc aag atc cgc cgg ctg tcg gcc tgc aag cag    1296
Ala Cys Ser Ala Ser Ser Lys Ile Arg Arg Leu Ser Ala Cys Lys Gln
        420                 425                 430 cag tga                                                             1302
Gln

<210> SEQ ID NO 6
<211> LENGTH: 433
<212> TYPE: PRT
<213> ORGANISM: Homo sapiens

<400> SEQUENCE: 6

Met Glu Val Val Asp Pro Gln Gln Leu Gly Met Phe Thr Glu Gly Glu
1               5                   10                  15

Leu Met Ser Val Gly Met Asp Thr Phe Ile His Arg Ile Asp Ser Thr
            20                  25                  30

Glu Val Ile Tyr Gln Pro Arg Arg Lys Arg Ala Lys Leu Ile Gly Lys
        35                  40                  45

Tyr Leu Met Gly Asp Leu Leu Gly Glu Gly Ser Tyr Gly Lys Val Lys
```

```
               50                  55                  60
Glu Val Leu Asp Ser Glu Thr Leu Cys Arg Arg Ala Val Lys Ile Leu
 65                  70                  75                  80

Lys Lys Lys Lys Leu Arg Arg Ile Pro Asn Gly Glu Ala Asn Val Lys
                 85                  90                  95

Lys Glu Ile Gln Leu Arg Arg Leu Arg His Lys Asn Val Ile Gln
                100                 105                 110

Leu Val Asp Val Leu Tyr Asn Glu Lys Gln Lys Met Tyr Met Val
                115                 120                 125

Met Glu Tyr Cys Val Cys Gly Met Gln Glu Met Leu Asp Ser Val Pro
130                 135                 140

Glu Lys Arg Phe Pro Val Cys Gln Ala His Gly Tyr Phe Cys Gln Leu
145                 150                 155                 160

Ile Asp Gly Leu Glu Tyr Leu His Ser Gln Gly Ile Val His Lys Asp
                165                 170                 175

Ile Lys Pro Gly Asn Leu Leu Leu Thr Thr Gly Thr Leu Lys Ile
                180                 185                 190

Ser Asp Leu Gly Val Ala Glu Ala Leu His Pro Phe Ala Ala Asp Asp
                195                 200                 205

Thr Cys Arg Thr Ser Gln Gly Ser Pro Ala Phe Gln Pro Pro Glu Ile
210                 215                 220

Ala Asn Gly Leu Asp Thr Phe Ser Gly Phe Lys Val Asp Ile Trp Ser
225                 230                 235                 240

Ala Gly Val Thr Leu Tyr Asn Ile Thr Thr Gly Leu Tyr Pro Phe Glu
                245                 250                 255

Gly Asp Asn Ile Tyr Lys Leu Phe Glu Asn Ile Gly Lys Gly Ser Tyr
                260                 265                 270

Ala Ile Pro Gly Asp Cys Gly Pro Pro Leu Ser Asp Leu Leu Lys Gly
                275                 280                 285

Met Leu Glu Tyr Glu Pro Ala Lys Arg Phe Ser Ile Arg Gln Ile Arg
290                 295                 300

Gln His Ser Trp Phe Arg Lys Lys His Pro Pro Ala Glu Ala Pro Val
305                 310                 315                 320

Pro Ile Pro Pro Ser Pro Asp Thr Lys Asp Arg Trp Arg Ser Met Thr
                325                 330                 335

Val Val Pro Tyr Leu Glu Asp Leu His Gly Ala Asp Glu Asp Glu Asp
                340                 345                 350

Leu Phe Asp Ile Glu Asp Asp Ile Ile Tyr Thr Gln Asp Phe Thr Val
                355                 360                 365

Pro Gly Gln Val Pro Glu Glu Glu Ala Ser His Asn Gly Gln Arg Arg
                370                 375                 380

Gly Leu Pro Lys Ala Val Cys Met Asn Gly Thr Glu Ala Ala Gln Leu
385                 390                 395                 400

Ser Thr Lys Ser Arg Ala Glu Gly Arg Ala Pro Asn Pro Ala Arg Lys
                405                 410                 415

Ala Cys Ser Ala Ser Ser Lys Ile Arg Arg Leu Ser Ala Cys Lys Gln
                420                 425                 430

Gln
```

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: "DJ698", an

```
                           artificially synthesized primer sequence

<400> SEQUENCE: 7
ggtccccgag gacgaagttg a                                              21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: "DJ673",
      an artificially synthesized primer sequence

<400> SEQUENCE: 8
accatcagca ccgtgactgg                                                20

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: "DJ703",
      an artificially synthesized primer sequence

<400> SEQUENCE: 9
tcgccggccg atgacaga                                                  18

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: "DJ674",
      an artificially synthesized primer sequence

<400> SEQUENCE: 10
aaggagacgg gaagaggagc ag                                             22

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: "DJ690",
      an artificially synthesized primer sequence

<400> SEQUENCE: 11
gaggaggggc aaggtgggt                                                 19

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: "DJ680",
      an artificially synthesized primer sequence

<400> SEQUENCE: 12
gtgtggcctc acggaaagga g                                              21

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: "DJ692", an
      artificially synthesized primer sequence
```

```
<400> SEQUENCE: 13
agctgggcct gtggtgtttg                                           20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: "DJ694", an
      artificially synthesized primer sequence

<400> SEQUENCE: 14
cagaggcccc tcggagtgtg                                           20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: "DJ695", an
      artificially synthesized primer sequence

<400> SEQUENCE: 15
gcctctgtcc ctggggtaga                                           20

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: "DJ693", an
      artificially synthesized primer sequence

<400> SEQUENCE: 16
tcagtcctct caatgcctgc tg                                        22

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: "DJ696", an
      artificially synthesized primer sequence

<400> SEQUENCE: 17
gcggggtccc ccttaggag                                            19

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: "DJ697", an
      artificially synthesized primer sequence

<400> SEQUENCE: 18
ctagcgcccg ctcaaccag                                            19

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: "DJ675", an
      artificially synthesized primer sequence

<400> SEQUENCE: 19
```

```
ggagctgggt cggaaaactg ga                                              22
```

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: "DJ702", an
      artificially synthesized primer sequence

<400> SEQUENCE: 20

```
tgctcccgtg ggacatcctg                                                 20
```

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: "DJ676", an
      artificially synthesized primer sequence

<400> SEQUENCE: 21

```
gtaagtgcgt ccccgtggtg                                                 20
```

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: "DJ677", an
      artificially synthesized primer sequence

<400> SEQUENCE: 22

```
gtggcatcca ggcgttgtcc                                                 20
```

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: "DJ705", an
      artificially synthesized primer sequence

<400> SEQUENCE: 23

```
gggaattcgg aacacaagga ag                                              22
```

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: "DJ649", an
      artificially synthesized primer sequence

<400> SEQUENCE: 24

```
atggaggtgg tggacccgc                                                  19
```

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: "DJ659", an
      artificially synthesized primer sequence

<400> SEQUENCE: 25

```
gttacggcac aaaaatgtca tcca                                            24
```

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: "DJ666", an
      artificially synthesized primer sequence

<400> SEQUENCE: 26
ggtgatggag tactgcgtgt g                                              21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: "DJ684", an
      artificially synthesized primer sequence

<400> SEQUENCE: 27
acatcgggaa ggggagctac g                                              21

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: "DJ660", an
      artificially synthesized primer sequence

<400> SEQUENCE: 28
ccgggcaccg tgaagtcctg                                                20

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: "DJ650", an
      artificially synthesized primer sequence

<400> SEQUENCE: 29
tcactgctgc ttgcaggcc                                                 19

<210> SEQ ID NO 30
<211> LENGTH: 17
<212> TYPE: DNA
<213> ORGANISM: Artificial Sequence
<220> FEATURE:
<223> OTHER INFORMATION: Description of Artificial Sequence: "DJ717", an
      artificially synthesized primer sequence

<400> SEQUENCE: 30
gcaggcggcc agcctca                                                   17

<210> SEQ ID NO 31
<211> LENGTH: 19
<212> TYPE: PRT
<213> ORGANISM: Homo sapiens

<400> SEQUENCE: 31

Cys Leu Ser Thr Lys Ser Arg Ala Glu Gly Arg Ala Pro Asn Pro Ala
 1               5                  10                  15

Arg Lys Ala

<210> SEQ ID NO 32

```
<211> LENGTH: 20
<212> TYPE: PRT
<213> ORGANISM: Homo sapiens

<400> SEQUENCE: 32

Cys Ile Arg Gln Ile Arg Gln His Ser Trp Phe Arg Lys Lys His Pro
 1               5                  10                  15

Pro Ala Glu Ala
            20

<210> SEQ ID NO 33
<211> LENGTH: 20
<212> TYPE: PRT
<213> ORGANISM: Homo sapiens

<400> SEQUENCE: 33

Cys Phe Glu Gly Asp Asn Ile Tyr Lys Leu Phe Glu Asn Ile Gly Lys
 1               5                  10                  15

Gly Ser Tyr Ala
            20

<210> SEQ ID NO 34
<211> LENGTH: 20
<212> TYPE: PRT
<213> ORGANISM: Homo sapiens

<400> SEQUENCE: 34

Cys His Arg Ile Asp Ser Thr Glu Val Ile Tyr Gln Pro Arg Arg Lys
 1               5                  10                  15

Arg Ala Lys Leu
            20

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: "DJ180", an
      artificially synthesized primer sequence

<400> SEQUENCE: 35
cgactcacta tagggagacc ca                                              22

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: "DJ181", an
      artificially synthesized primer sequence

<400> SEQUENCE: 36
cctcgagaat taccctcact aa                                              22

<210> SEQ ID NO 37
<211> LENGTH: 17
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 37
tggatctaca ctccggc                                                    17
```

```
<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: an
      artificially synthesized primer sequence

<400> SEQUENCE: 38
attttactgg ctggcacttg                                              20

<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: "LK E1", an
      artificially synthesized primer sequence

<400> SEQUENCE: 39
gatgaattcg ggtccagcat ggaggtggtg gac                               33

<210> SEQ ID NO 40
<211> LENGTH: 60
<212> TYPE: DNA
<213> ORGANISM: Artificial Sequence
<220> FEATURE:
<223> OTHER INFORMATION: Description of Artificial Sequence: "LK E2", an
      artificially synthesized primer sequence

<400> SEQUENCE: 40
gatgaattct tagaggtctt cttctgagat gagcttctgc tcctgctgct tgcaggccga  60

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: an
      artificially synthesized c-Myc partial sequence

<400> SEQUENCE: 41

Glu Gln Lys Leu Ile Ser Glu Glu Asp Leu
 1               5                  10

<210> SEQ ID NO 42
<211> LENGTH: 63
<212> TYPE: DNA
<213> ORGANISM: Artificial Sequence
<220> FEATURE:
<223> OTHER INFORMATION: Description of Artificial Sequence: "LK E4", an
      artificially synthesized primer sequence

<400> SEQUENCE: 42
gatgggccct tacagggagg catagtcagg cacatcatat gggtactgct gcttgcaggc  60
cga                                                                63

<210> SEQ ID NO 43
<211> LENGTH: 48
<212> TYPE: DNA
<213> ORGANISM: Artificial Sequence
<220> FEATURE:
<223> OTHER INFORMATION: Description of Artificial Sequence: "LK E5", an
      artificially synthesized primer sequence

<400> SEQUENCE: 43
gatgaattct tagtgatggt gatggtgatg ctgctgcttg caggccga               48
```

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: an artificially synthesized HA partial sequence

<400> SEQUENCE: 44

Tyr Pro Tyr Asp Val Pro Asp Tyr Ala Ser Leu
 1               5                  10

<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence: "LK D176N", an artificially synthesized primer sequence

<400> SEQUENCE: 45
attgtgcaca agaacatcaa gccgggg                                27

<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence: "LK W308C", an artificially synthesized primer sequence

<400> SEQUENCE: 46
cggcagcaca gctgcttccg gaagaaa                                27

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: "LK L67P", an artificially synthesized primer sequence

<400> SEQUENCE: 47
gtgaaggagg tgccggactc ggagacg                                27

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence: "LK KI1", an artificially synthesized primer sequence

<400> SEQUENCE: 48
aggagggccg tcatcatcct caagaag                                27